United States Patent
Machida et al.

(10) Patent No.: US 6,917,694 B1
(45) Date of Patent: Jul. 12, 2005

(54) SURFACE SHAPE RECOGNITION APPARATUS AND METHOD

(75) Inventors: Katsuyuki Machida, Kanagawa (JP); Satoshi Shigematsu, Kanagawa (JP); Hiroki Morimura, Kanagawa (JP); Hakaru Kyuragi, Tokyo (JP); Takuya Adachi, Kanagawa (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 09/573,615

(22) Filed: May 17, 2000

(30) Foreign Application Priority Data

May 17, 1999 (JP) .......................................... 11-135660

(51) Int. Cl.[7] .............................. G06K 9/00; G06F 7/04
(52) U.S. Cl. ...................... 382/124; 340/5.53; 340/5.83
(58) Field of Search ................................ 382/115, 116, 382/124, 125, 126, 127; 340/5.53, 5.83

(56) References Cited

U.S. PATENT DOCUMENTS

| | | | | |
|---|---|---|---|---|
| 4,135,147 A | * | 1/1979 | Riganati et al. | ............ 382/125 |
| 4,581,760 A | * | 4/1986 | Schiller et al. | ............. 382/124 |
| 4,641,350 A |   | 2/1987 | Bunn | |

(Continued)

FOREIGN PATENT DOCUMENTS

| | | | | |
|---|---|---|---|---|
| JP | 61-221883 | | 10/1986 | |
| JP | 01088883 A | * | 4/1989 | ........... G06F/15/62 |
| JP | 04178884 A | * | 6/1992 | ........... G06F/15/62 |
| JP | 5-061965 | | 3/1993 | |
| JP | 06-274602 | | 9/1994 | |
| JP | 7-168930 | | 7/1995 | |
| JP | 07220075 A | * | 8/1995 | ............. G06T/7/00 |
| JP | 09-062840 | | 3/1997 | |
| JP | 10-143663 | | 5/1998 | |
| JP | 10-255050 | | 9/1998 | |
| JP | 11096358 A | * | 4/1999 | ............. G06T/7/00 |
| WO | WO 00/49944 | | 8/2000 | |

OTHER PUBLICATIONS

Yahagi et al: "Moving–Window Algorithm for Fast Fingerprint Verification" Southeastcon '90. Proceedings., IEEE , Apr. 1–4, 1990 pp.: 343–348 vol. 1.*

(Continued)

Primary Examiner—Amelia M. Au
Assistant Examiner—Ryan J. Hesseltine
(74) Attorney, Agent, or Firm—Blakaly Sokoloff Taylor & Zafman

(57) ABSTRACT

A surface shape recognition apparatus includes detection circuit, comparison circuit, storage circuit, and control circuit. The detection circuit electrically detects a surface shape pattern in a partial region of the target collation surface of an object using a plurality of sensor elements and outputs detection data representing the surface shape pattern. The comparison circuit compares the detection data from the detection circuit with predetermined collation data and outputs a comparison result. The storage circuit stores template data representing the surface shape pattern of the entire target collation surface, the template data being obtained from the object in advance. The control circuit partially reads out, as collation data, the template data stored in the storage circuit from an arbitrary position, outputs the collation data to the comparison circuit, and performs determination for authentication between the template data and the object on the basis of the comparison result from the comparison circuit. A surface shape recognition method is also disclosed.

91 Claims, 11 Drawing Sheets

U.S. PATENT DOCUMENTS

| | | | | |
|---|---|---|---|---|
| 4,933,976 A | * | 6/1990 | Fishbine et al. | 382/127 |
| 5,040,223 A | * | 8/1991 | Kamiya et al. | 382/127 |
| 5,054,090 A | | 10/1991 | Knight et al. | |
| 5,177,802 A | * | 1/1993 | Fujimoto et al. | 382/124 |
| 5,210,797 A | * | 5/1993 | Usui et al. | 382/126 |
| 5,559,504 A | * | 9/1996 | Itsumi et al. | 340/5.53 |
| 5,878,157 A | * | 3/1999 | Mukohzaka | 382/124 |
| 5,982,913 A | * | 11/1999 | Brumbley et al. | 382/124 |
| 6,031,942 A | * | 2/2000 | Nakayama | 382/284 |
| 6,060,756 A | * | 5/2000 | Machida et al. | 257/415 |
| 6,097,035 A | * | 8/2000 | Belongie et al. | 250/556 |
| 6,241,288 B1 | * | 6/2001 | Bergenek et al. | 283/67 |
| 6,256,022 B1 | * | 7/2001 | Manaresi et al. | 345/174 |
| 6,289,114 B1 | * | 9/2001 | Mainguet | 382/124 |
| 6,333,989 B1 | * | 12/2001 | Borza | 382/124 |
| 6,356,649 B2 | * | 3/2002 | Harkless et al. | 382/115 |
| 6,408,087 B1 | * | 6/2002 | Kramer | 382/124 |
| 6,546,122 B1 | * | 4/2003 | Russo | 382/125 |

OTHER PUBLICATIONS

"A Study on the Structure of a Smart Card with the Function to Verify the Holder", Technical Report of IEICE, OFS92–32, pp. 25–30 (1992).

"A 390dpi Live Fingerprint Imager Based on Feedback Capacitive Sensing Scheme" 1997 IEEE International Solid–State Circuits Conference, pp. 200–201 (1997).

"A 15×15–mm single–chip fingerprint sensor and identifier using pixel–parallel processing", 1999 IEEE International Solid–State Circuits Conference (1991).

Jeong–Woo Lee, Dong–Jin Min, Jiyoun Kim, and Wonchan Kim, "A 600–dpi Capacitive Fingerprint Sensor Chip and Image–Synthesis Technique", IEEE Journal of Solid–State Circuit, vol. 34, No. 4, pp. 469–475 Apr. 1999.

* cited by examiner

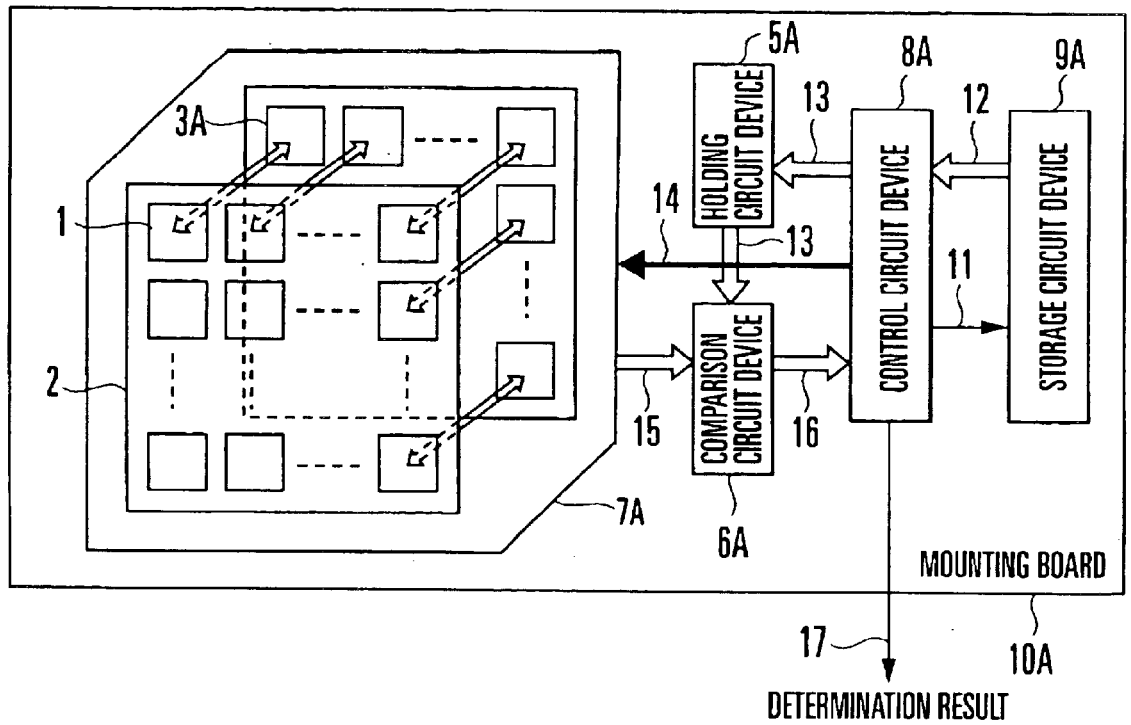
F I G. 5
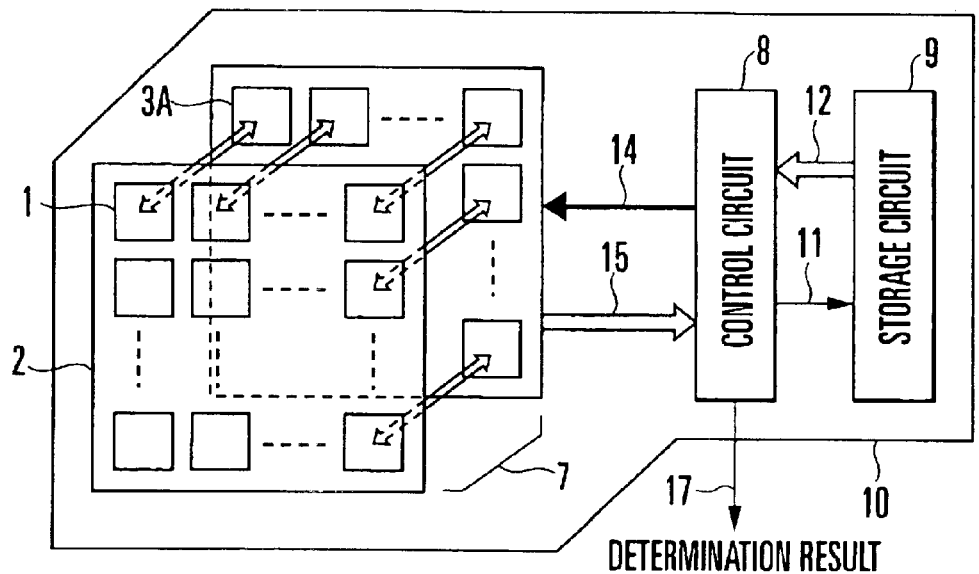
F I G. 6

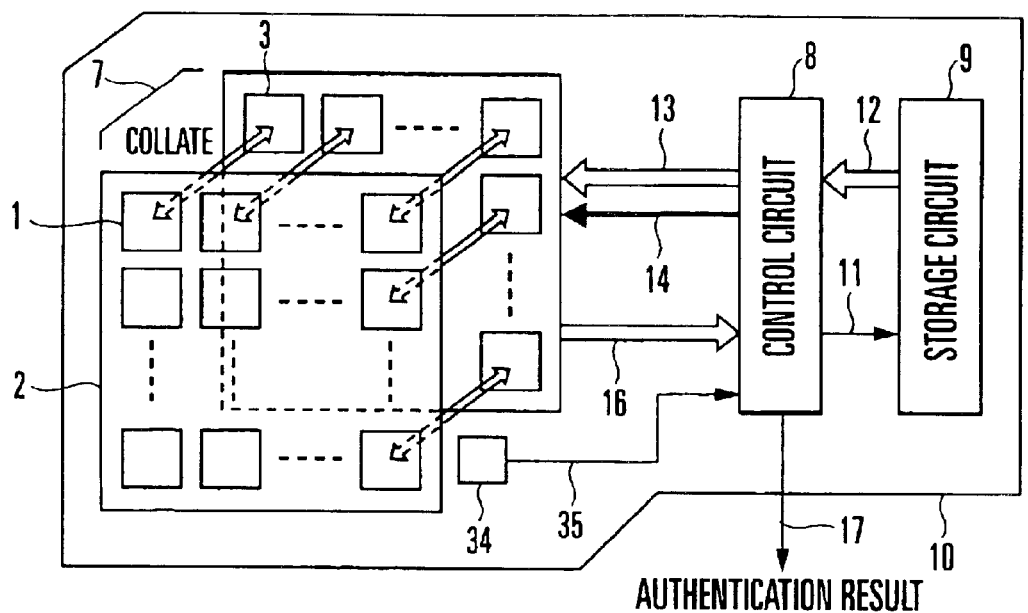
F I G. 16
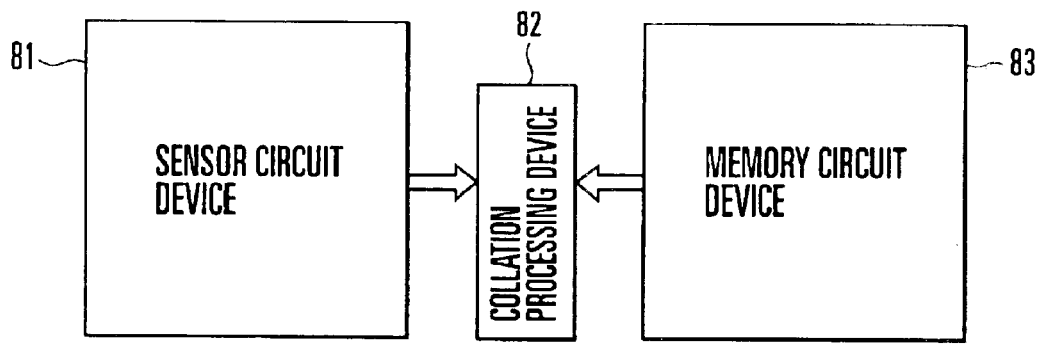
F I G. 17
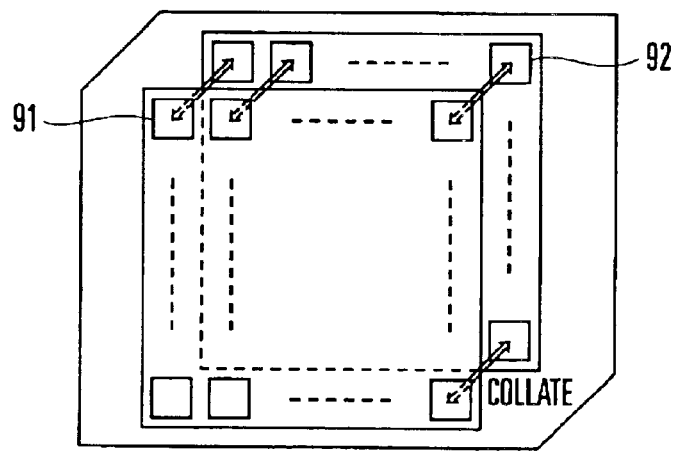
F I G. 18

SURFACE SHAPE RECOGNITION APPARATUS AND METHOD

BACKGROUND OF THE INVENTION

The present invention relates to a sensor for sensing the surface shape of a human finger or animal nose having a small three-dimensional (i.e., surface shape) pattern, and a collation/recognition technique.

In the social environment of today where the information-oriented society is developing, the security technology has taken a growing interest. For example in the information-oriented society, a personal authentication technology for constructing an electronic money system is an important key. In fact, authentication technologies for implementing preventive measures against burglary and illicit use of cards are under active research and development (for example, Yoshimasa Shimizu, "A Study on the Structure of a Smart Card with the Function to Verify the Holder", Technical Report of IEICE, OFS92-32, pp. 25–30, (1992)). Such authentication techniques include various schemes using a fingerprint or voiceprint. Especially, many fingerprint authentication techniques have been developed.

Fingerprint authentication schemes are roughly classified into optical read schemes, schemes using human electrical characteristics, and schemes of detecting a three-dimensional pattern on the skin surface of a fingertip and converting it into an electrical signal. In an optical read scheme, fingerprint data is received mainly using light reflection and a CCD and collated (for example, Japanese Patent Laid-Open No. 61-221883). A scheme using a piezo-electric thin film to read the pressure difference on a finger skin surface has also been developed (for example, Japanese Patent Laid-Open No. 5-61965). As a scheme of converting a change in electrical characteristics due to contact of skin into an electrical signal distribution to detect the fingerprint, an authentication scheme of detecting a resistance change amount or capacitance change amount using a pressure sensitive sheet has been proposed (for example, Japanese Patent Laid-Open No. 7-168930).

However, of the above techniques, the scheme using light is hard to achieve size reduction and versatility, and its application purpose is limited. The scheme of sensing a three-dimensional pattern on the skin surface of a fingertip can hardly be put into practical use and is poor in reliability because of special materials and difficulty in working. A capacitive fingerprint sensor using an LSI manufacturing technology has also been proposed (for example, Marco Tartagni and Roberto Guerrieri, A 390 dpi Live Fingerprint Imager Based on Feedback Capacitive Sensing Scheme, 1997 IEEE International Solid-State Circuits Conference, pp. 200–201 (1997)).

In this method, small sensors two-dimensionally arrayed on an LSI chip detect a three-dimensional pattern of a skin using a feedback electrostatic capacitance scheme. For this capacitive sensor, two plates are formed on the uppermost layer of LSI interconnections, and a passivation film is formed thereon. The skin surface functioning as a third plate is spaced apart by an insulating layer formed by air. Sensing is performed on the basis of the distance difference, thereby detecting the fingerprint. As characteristic features of this structure, no special interface is required, and the size can be reduced, unlike the conventional optical scheme.

However, such a conventional recognition apparatus has a large surface area occupied by the sensor portion and suffers several problems.

As the first problem, cost of a system construction becomes high when the yield of LSI development is taken into consideration. As the second problem, although an apparatus with a small contact area is hard to break and can stand mechanical stress, the apparatus readily breaks from the viewpoint of reliability because of the large volume. More specifically, in a conventional recognition apparatus, a sensor circuit device 81 whose sensor portion has a large surface area, a collation processing circuit device 82, and a memory circuit device 83 are mounted as a multi-chip structure to perform authentication, as shown in FIG. 17.

In this case, for example, authentication processing for a fingerprint is done using a sensor having a large finger contact area, and the image area used for authentication equals the contact area. Hence, the area at the sensor-circuit device 81 increases to impede cost reduction. Even when not multi-chip mounting but one-chip mounting is employed, the chip area inevitably increases. Obviously, the cost increases from the viewpoint of yield of LSIs, and the structure also poses a problem of reliability.

As illustrated in FIG. 18, a scheme has also been proposed, in which a number of pixel circuits 92 are provided to oppose a number of sensor elements 91, respectively, and a sensor circuit for driving a sensor element 91, a memory circuit for storing collation data, and a collation processing circuit are mounted in a corresponding pixel circuit 92, thereby integrating the authentication unit and sensor (for example, S. Shigematsu, H. Morimura, Y. Tanabe, and K. Machida, "A 15×15-mm2 single-chip fingerprint sensor and identifier using pixel-parallel processing", 1999 IEEE International Solid-State Circuits Conference, (1991)).

In this case, pixel circuits in number corresponding to the finger contact area are necessary. The chip becomes large depending on the mounting area. For this reason, the cost cannot be reduced from the viewpoint of yield of LSIs.

SUMMARY OF THE INVENTION

The present invention has been made in consideration of the above problems, and has as its object to provide a surface shape recognition processing apparatus capable of recognizing, using a relatively small detection area, the surface shape of a human finger or animal nose having a small three-dimensional pattern and ensuring cost reduction and high reliability.

In order to achieve the above object, according to the present invention there is provided a surface shape recognition apparatus for detecting a shape of a target collation surface of an object having a small surface shape pattern and comparing and collating the shape with predetermined data to authenticate the object, comprising detection means for electrically detecting the surface shape pattern in a partial region of the target collation surface of the object using a plurality of sensor elements and outputting detection data representing the surface shape pattern, comparison means for comparing the detection data from the detection means with predetermined collation data and outputting a comparison result, storage means for storing template data representing the surface shape pattern of the entire target collation surface, the template data being obtained from the object in advance, and control means for partially reading out, as collation data, the template data stored in the storage means from an arbitrary position, outputting the collation data to the comparison means, and performing determination for authentication between the template data and the object on the basis of the comparison result from the comparison means.

BRIEF DESCRIPTION OF THE DRAWINGS

FIG. 5 is a block diagram of a surface shape recognition apparatus according to the fourth embodiment;

FIG. 6 is a block diagram of a surface shape recognition apparatus according to the fifth embodiment;

FIG. 16 is a block diagram of a surface shape recognition apparatus according to the 12th embodiment;

FIG. 17 is an explanatory view showing an arrangement of a conventional surface shape recognition apparatus; and FIG. 18 is an explanatory view showing another arrangement of the conventional surface shape recognition apparatus.

DESCRIPTION OF THE PREFERRED EMBODIMENTS

The present invention will be described next with reference to the accompanying drawings.

Figure 1A:
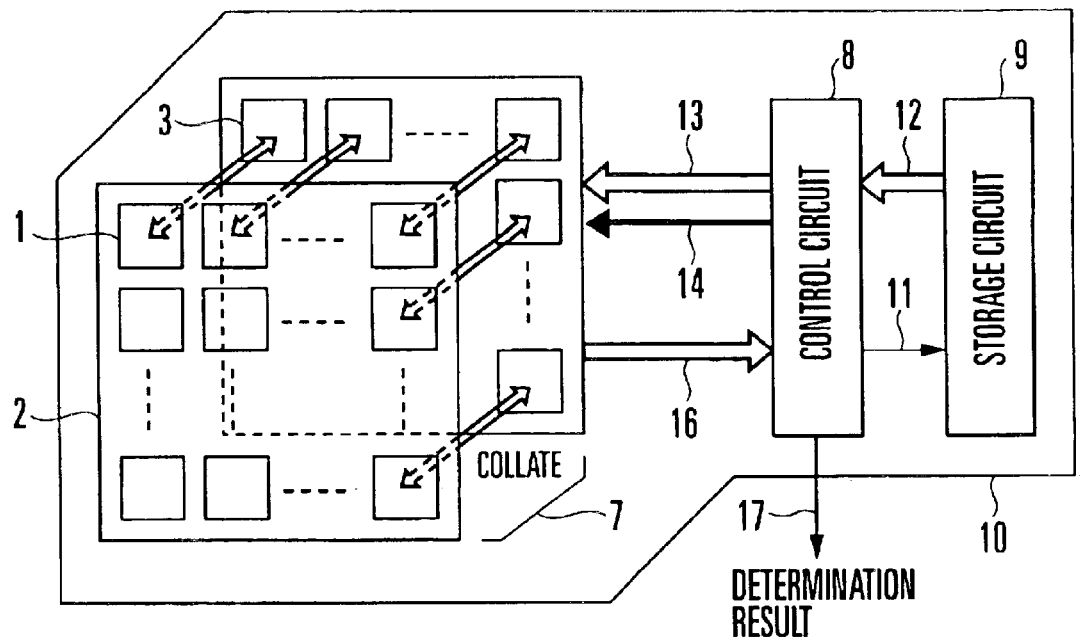
FIGS. 1A and 1B are block diagrams of a surface shape recognition apparatus according to the first embodiment.
Figure 1B:
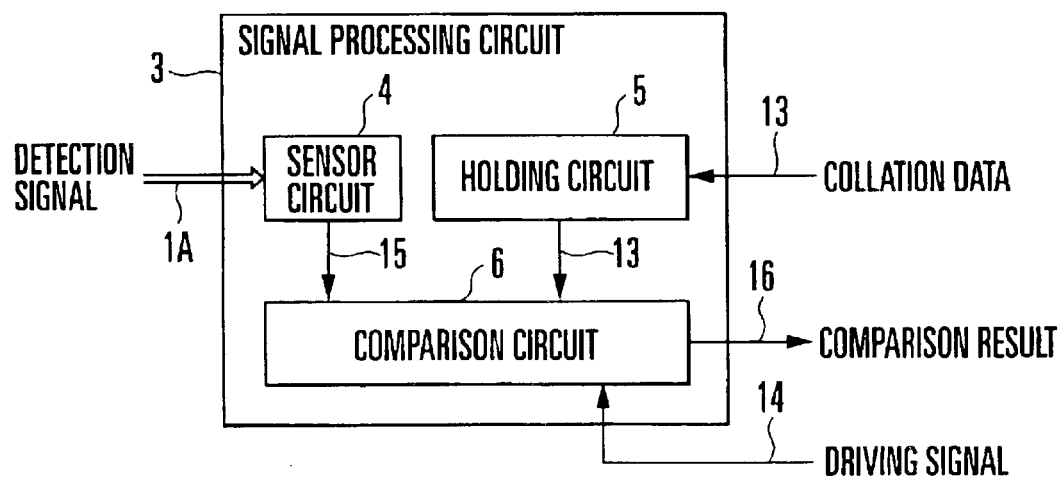

FIGS. 1A and 1B show a surface shape recognition apparatus according to the first embodiment of the present invention. FIG. 1A shows the entire apparatus, and FIG. 1B shows the signal processing circuit portion. In this embodiment, circuit portions are mounted on a one-chip semiconductor integrated circuit device 10 by a semiconductor integration technology. Referring to FIG. 1A, a surface shape detection circuit 7 comprises a sensor 2 (semiconductor sensor) having a number of sensor elements 1 arrayed in a matrix, and signal processing circuits 3 prepared closely in correspondence with the sensor elements 1, respectively.

Each sensor element 1 is a circuit element for converting a three-dimensional pattern of the target collation surface of an object into an electrical signal and is formed in the sensor 2 using the semiconductor integration technology. In this case, the number of sensor elements 1 is enough to detect not the entire target collation surface but only part thereof. For this reason, the surface area occupied by all the sensor elements 1 is smaller than that of the prior art. As shown in FIG. 1B, each signal processing circuit 3 has a sensor circuit 4 for processing a detection signal 1A from the corresponding sensor element 1 and outputting detection data 15, a holding circuit 5 for holding collation data 13 to be compared with the detection data 15, and a comparison circuit 6 for controlling the sensor circuit 4 and holding circuit 5 on the basis of a driving signal 14, comparing the detection data 15 from the sensor circuit 4 with the collation data 13 from the holding circuit 5, and outputting a comparison result 16.

A storage circuit 9 for storing entire template data in advance, and a control circuit 8 for reading part of the template data, i.e., collation data 12 from the storage circuit 9 and outputting it to the surface shape detection circuit 7 as the collation data 13 and determines authentication for the object on the basis of the comparison result 16 from the surface shape detection circuit 7 and outputting a determination result 17 are also provided independently of the surface shape detection circuit 7.

The sensor element 1 and sensor circuit 4 correspond to a detection means for electrically detecting the three-dimensional pattern in a partial region of the target collation surface of an object and outputting detection data representing the three-dimensional pattern. The holding circuit 5 and comparison circuit 6 correspond to a comparison means for comparing the detection data from the detection means with predetermined collation data and outputting the comparison result. The storage circuit 9 corresponds to a storage means for storing template data representing the three-dimensional pattern of the entire target collation surface, which is obtained from the object in advance. The control circuit 8 corresponds to a control means for partially reading out, as collation data, the template data stored in the storage means from an arbitrary position, outputting the collation data to the comparison means, and determining authentication for the object on the basis of the comparison result from the comparison means.

In this embodiment, as the sensor element 1, a capacitive sensor is used, which detects the three-dimensional pattern on the target collation surface of the object utilizing a fact that the capacitance changes when the sensor element comes into contact with the target collation surface. A sensor of any other scheme, e.g., a resistance type may be used as far as it can detect the three-dimensional pattern of the target collation surface. For example, to recognize a human fingerprint, the total surface area (detection area) of all sensor elements 1 is 10 mm square or less. Each signal processing circuit 3 for comparing and collating collation data with detection data detected by a corresponding sensor element 1 has a size of 50 to 100 μm square. A RAM (Random Access Memory) is used as the holding circuit 5.

A nonvolatile memory is used as the storage circuit 9. For example, a ROM (Read Only Memory) or a programmable EEPROM or flash memory may be used as the storage circuit 9. The storage circuit 9 need not always use a nonvolatile memory depending on the system power supply method, and is selected in accordance with the system. The storage circuit 9 stores data obtained in advance from the entire target collation surface of the object as template data. For, e.g., a fingerprint, all fingerprint data in an area about 20 mm square are ensured.

The operation of this embodiment will be described next with reference to FIGS. 1A to 2B.

Figure 2A:
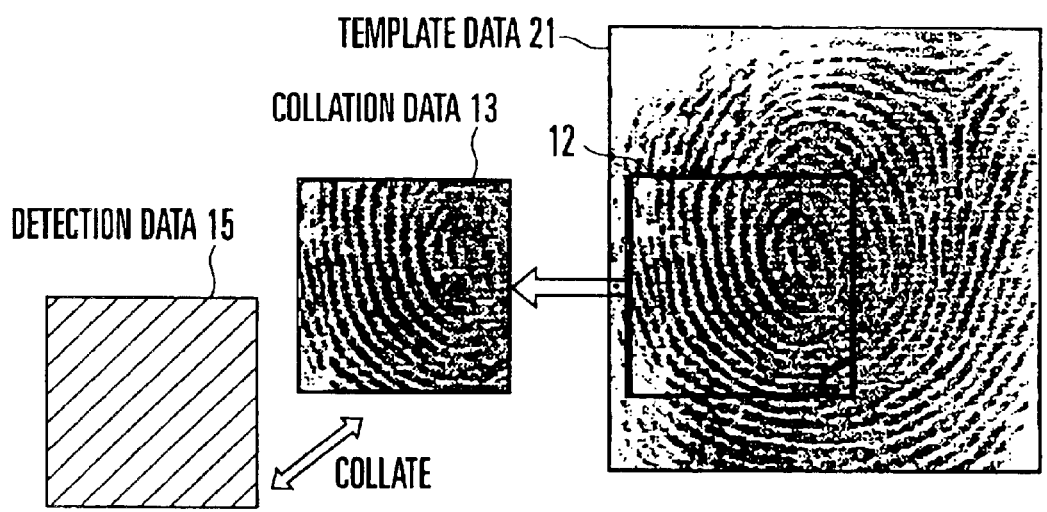
FIGS. 2A and 2B are an explanatory view and flow chart, respectively, showing the basic recognition operation of the first embodiment.
Figure 2B:
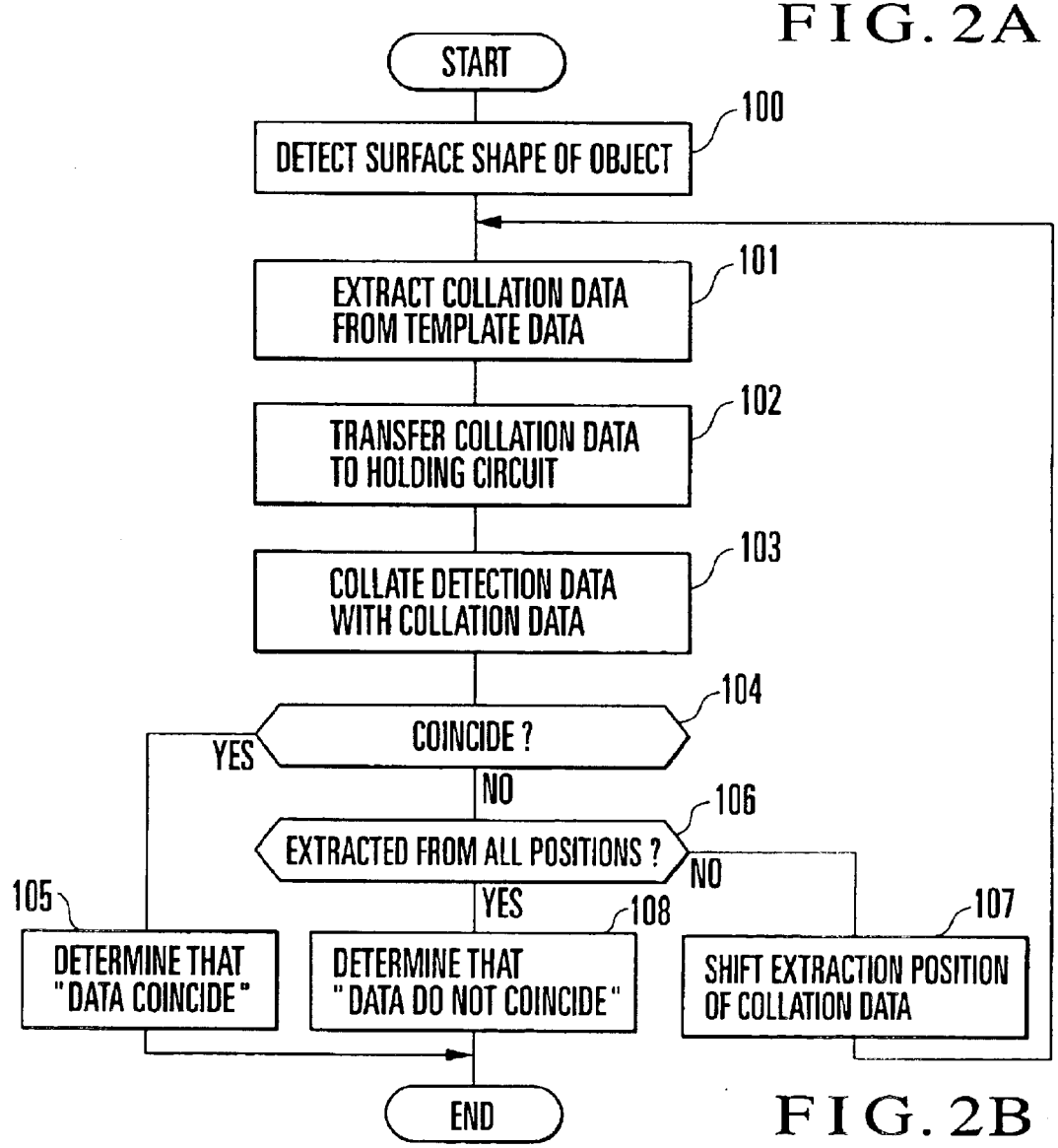

FIGS. 2A and 2B show the basic recognition operation of this embodiment. FIG. 2A shows the schematic operation, and FIG. 2B shows the flow chart. Generally, to recognize an object, detection data obtained from the object is compared with template data as a collation standard, and recognition and determination are done on the basis of the comparison result. Conventionally, detection data representing the entire target collation surface of an object is collated. However, the entire target collation surface of an object need not be collated because the target collation surface has a complex three-dimensional pattern. In the present invention, based on this fact, using the detection data 15 obtained from part of the target collation surface of an object, a pattern which coincides with the detection data 15 is searched from entire template data 21.

More specifically, the collation data 12 for collation are sequentially extracted from different positions of the template data 21, and each extracted collation data 13 (12) is compared and collated with the detection data 15. As a region where the collation data 13 (12) is to be extracted from the template data 21, a region corresponding to the target collation surface of the object detected by the surface shape detection circuit 7 must be extracted. In this case, a means for positioning the object may be prepared to extract the collation data 13 (12) from a corresponding region of the template data 21.

In this embodiment, as shown in FIG. 2B, first, the driving signal 14 for instructing detection of the target collation surface of the object is output from the control circuit 8 to the signal processing circuit 3 (step 100). In the signal processing circuit 3, on the basis of the driving signal 14, the sensor circuit 4 processes the detection signal from a corresponding sensor element 1 and outputs the detection data 15.

The control circuit 8 extracts the collation data 12 from an arbitrary position of the template data 21 stored in the storage circuit 9 (step 101) and distributes the collation data 12, as the collation data 13, to the signal processing circuits 3 in the surface shape detection circuit 7 in units of pixels corresponding to the sensor elements 1 (step 102).

In each signal processing circuit 3, the holding circuit 5 receives and holds the distributed collation data 13. The comparison circuit 6 compares and collates the detection data 15 from the sensor circuit 4 with the collation data 13 from the holding circuit 5 and outputs the comparison result 16 in units of pixels (step 103).

After that, the control circuit 8 totalizes the comparison results 16 from the signal processing circuits 3 and determines authentication for the object using a similarity formed from a predetermined statistic amount such as a total collation rate (step 104).

If determination for authentication shows coincidence between the two data (YES in step 104), it is determined that the object coincides with the template data 21 (step 105), and the series of collation processes are ended.

If determination for authentication indicates that the two data do not coincide (NO in step 104), it is determined whether the collation data 13 has been extracted from all positions of the template data 21 (step 106). If an unextracted position still remains (NO in step 106), the collation data extraction position is shifted to the next position (step 107). The flow returns to step 102 to compare the collation data 13 extracted from the next position with the detection data 15.

If extraction from all positions is ended in step 106 (YES in step 106), it is determined that the object does not coincide with the template data 21, and the series of collation processes are ended.

As described above, according to this embodiment, the surface area occupied by all the sensor elements 1 can be reduced, and the yield in the process of manufacturing semiconductor integrated circuit devices can be increased. For this reason, cost can be reduced, and high reliability can be ensured, unlike the conventional large-area device. Hence, according to the present invention, the surface shape of a human finger or animal nose having a small three-dimensional pattern can be recognized using a relatively small surface area, and cost reduction and high reliability can be ensured.

Figure 3:
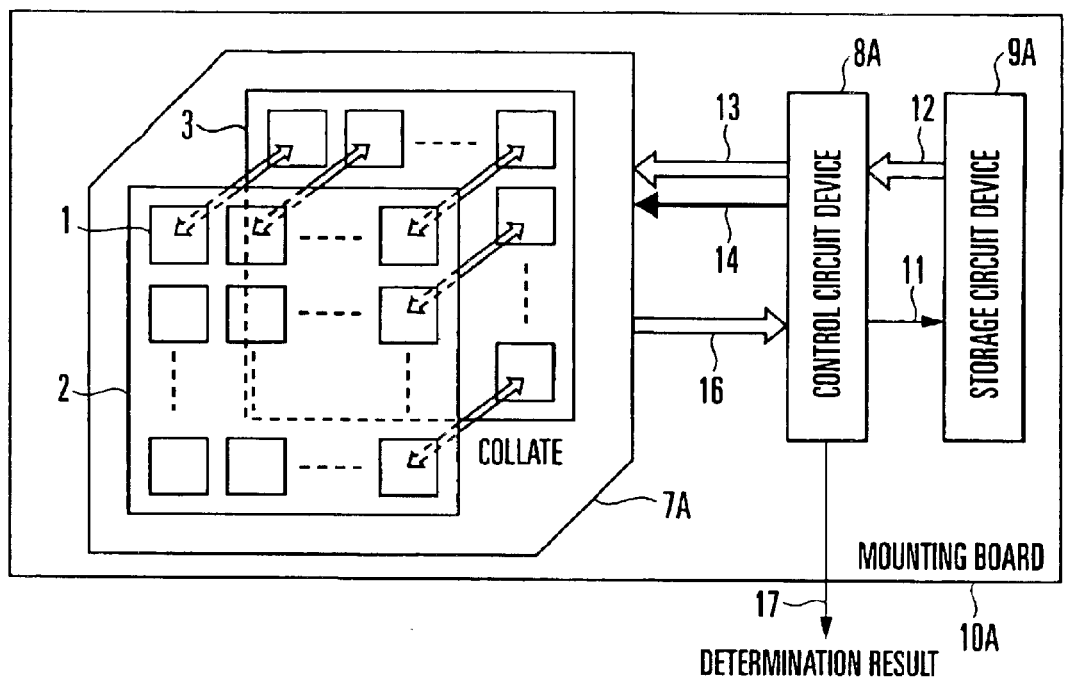
FIG. 3 is a block diagram of a surface shape recognition apparatus according to the second embodiment;.

The second embodiment of the present invention will be described next with reference to FIG. 3.

In the first embodiment (FIG. 1), the circuit portions are mounted on a one-chip semiconductor integrated circuit device. However, the circuit portions may be constructed by independent chips and arranged on one mounting board. In this embodiment, as shown in FIG. 3, a surface shape recognition apparatus is constructed by three chips: a surface shape detection circuit device 7A, control circuit device 8A, and storage circuit device 9A, and these chips are integrally arranged on one mounting board 10A (multi-chip structure). The surface shape detection circuit device 7A, control circuit device 8A, and storage circuit device 9A correspond to the surface shape detection circuit 7, control circuit 8, and storage circuit 9 in FIG. 1, respectively, and a detailed description of the operation will be omitted.

According to this embodiment, the same functions and effects as in the first embodiment can be obtained. Especially, since the storage circuit 9 which has a relatively high degree of integration and therefore readily decreases the yield is formed on a chip independently of the remaining circuits, the yield in the process of manufacturing the entire surface shape recognition apparatus can be improved, and cost can be reduced. When the storage circuit 9 is formed on a separate chip, the memory capacity can be increased, and the degree of freedom of recognition scheme increases because no limitations are imposed on the manufacturing process, unlike a one-chip structure.

The third embodiment of the present invention will be described below with reference to FIGS. 4A and 4B.

Figure 4A:
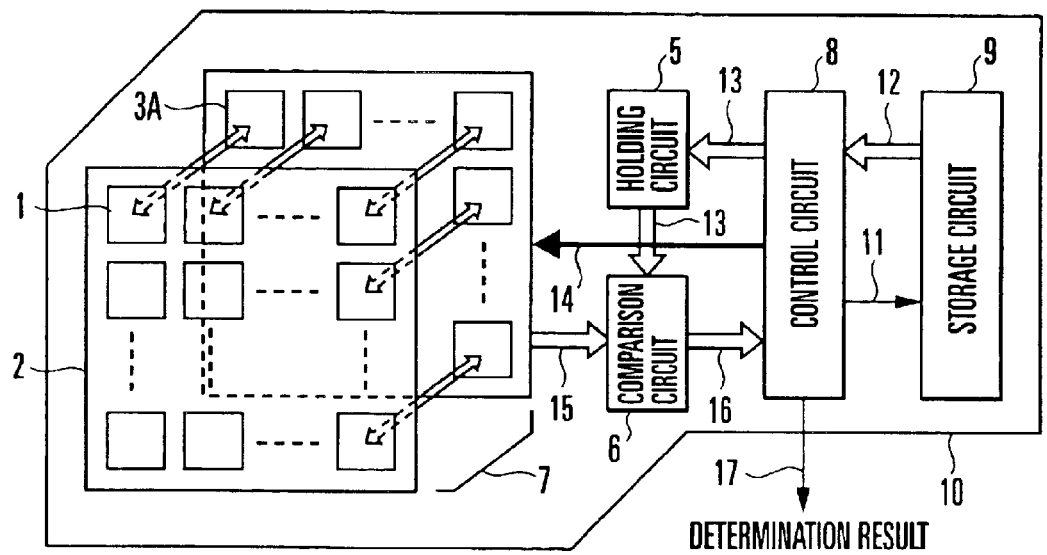
FIG. 4 is a block diagram of a surface shape recognition apparatus according to the third embodiment.
Figure 4B:
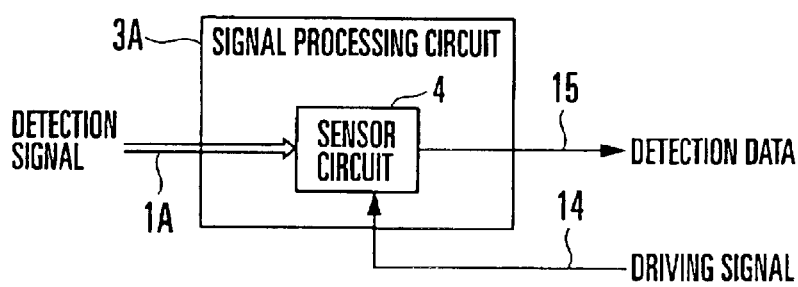

FIGS. 4A and 4B show a surface shape recognition apparatus according to the third embodiment of the present invention. FIG. 4A shows the entire apparatus, and FIG. 4B shows a signal processing circuit. In the first embodiment (FIG. 1), each signal processing circuit 3 in the surface shape detection circuit 7 has the sensor circuit 4, holding circuit 5, and comparison circuit 6. In this embodiment, a holding circuit 5 and comparison circuit 6 are arranged outside a surface shape detection circuit 7. Hence, as shown in FIG. 4B, each signal processing circuit 3A has only a sensor circuit 4 which processes a detection signal 1A from a corresponding sensor element 1 and outputs detection data 15 on the basis of a driving signal 14 from a control circuit 8.

The detection data 15 from each signal processing circuit 3A is input to the comparison circuit 6 and compared with collation data 13 from the holding circuit 5 in units of pixels. A comparison result 16 is output to the control circuit 8 in units of pixels. The control circuit 8 performs determination for authentication on the basis of the comparison result 16, as in the first embodiment.

Since the holding circuit 5 and comparison circuit 6 are arranged independently of the signal processing circuit 3A, the holding circuit 5 and comparison circuit 6 can be concentrated to make the entire surface shape recognition apparatus compact, in addition to the same functions and effects as in the first embodiment. In addition, the authentication algorithm in the comparison circuit 6 can be easily changed. Furthermore, the area occupied by the signal processing circuits 3A decreases, and accordingly, the mounting density of the sensor elements 1 can increase, and the surface area of the sensor 2 can be reduced.

The fourth embodiment of the present invention will be described below with reference to FIG. 5.

In the third embodiment (FIG. 4), the circuit portions are mounted on a one-chip semiconductor integrated circuit device. However, the circuit portions may be constructed by independent chips and arranged on one mounting board. In this embodiment, as shown in FIG. 5, a surface shape recognition apparatus is constructed by five chips: a surface shape detection circuit device 7A, holding circuit device 5A, comparison circuit device 6A, control circuit device 8A, and storage circuit device 9A, and these chips are integrally arranged on one mounting board 10A (multi-chip structure). The surface shape detection circuit device 7A, holding circuit device 5A, comparison circuit device 6A, control circuit device 8A, and storage circuit device 9A correspond to the surface shape detection circuit 7, holding circuit 5, comparison circuit 6, control circuit 8, and storage circuit 9 in FIG. 1, respectively, and a detailed description of the operation will be omitted.

According to this embodiment, the same functions and effects as in the third embodiment can be obtained. Especially, since the storage circuit 9 which has a relatively high degree of integration and therefore readily decreases the yield is formed on an independent chip, the yield in the process of manufacturing the entire surface shape recognition apparatus can be improved, and cost can be reduced. When the storage circuit 9 is formed on a separate chip, the memory capacity can be increased, and the degree of freedom of recognition scheme increases because no limitations are imposed on the manufacturing process, unlike a one-chip structure.

The fifth embodiment of the present invention will be described below with reference to FIG. 6.

In the third embodiment, the holding circuit 5 and comparison circuit 6 are arranged independently of the surface shape detection circuit 7. The processing operation by the comparison circuit 6 may be performed in the control circuit 8. Each signal processing circuit 3A of a surface shape detection circuit 7 has the same arrangement as in FIG. 4B. More specifically, as shown in FIG. 6, detection data 15A from each signal processing circuit 3A in the surface shape detection circuit 7 is input to a control circuit 8 and compared with collation data 13 read out from a storage circuit 9 in units of pixels, and determination for authentication is done on the basis of the comparison result. Since the holding circuit 5 can be omitted, the entire surface shape recognition apparatus can be made compact, in addition to the same functions and effects as in the first embodiment.

Figure 7:
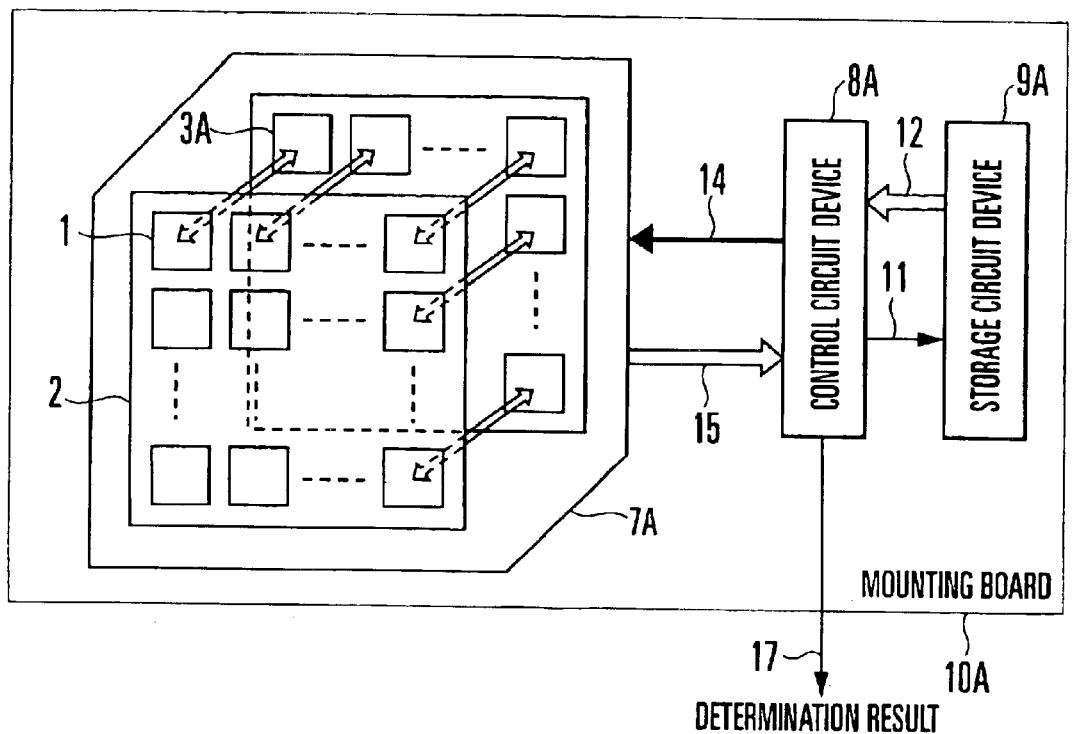
FIG. 7 is a block diagram of a surface shape recognition apparatus according to the sixth embodiment.

The sixth embodiment of the present invention will be described below with reference to FIG. 7.

In the fifth embodiment (FIG. 6), the circuit portions are mounted on a one-chip semiconductor integrated circuit device. However, the circuit portions may be constructed by independent chips and arranged on one mounting board. In this embodiment, as shown in FIG. 7, a surface shape recognition apparatus is constructed by three chips: a surface shape detection circuit device 7A, control circuit device 8A, and storage circuit device 9A, and these chips are integrally arranged on one mounting board 10A (multi-chip structure). The surface shape detection circuit device 7A, control circuit device 8A, and storage circuit device 9A correspond to the surface shape detection circuit 7, control circuit 8, and storage circuit 9 in FIG. 1, respectively, and a detailed description of the operation will be omitted.

According to this embodiment, the same functions and effects as in the fifth embodiment can be obtained. Especially, since the storage circuit 9 which has a relatively high degree of integration and therefore readily decreases the yield is formed on an independent chip, the yield in the process of manufacturing the entire surface shape recognition apparatus can be improved, and cost can be reduced. When the storage circuit 9 is formed on a separate chip, the memory capacity can be increased, and the degree of freedom of recognition scheme increases because no limitations are imposed on the manufacturing process, unlike a one-chip structure.

In the above description, data representing the entire target collation surface of the object must be used as template data. For this purpose, template data is generated in advance using a sensor such as a large semiconductor sensor or optical sensor capable of detecting the entire target collation surface of the object. The template data representing the entire target collation surface of the object may be generated by combining a plurality of data obtained by divisionally detecting the target collation surface of the object using a small sensor.

The seventh embodiment of the present invention will be described below with reference to FIGS. 8 and 9.

Figure 8:
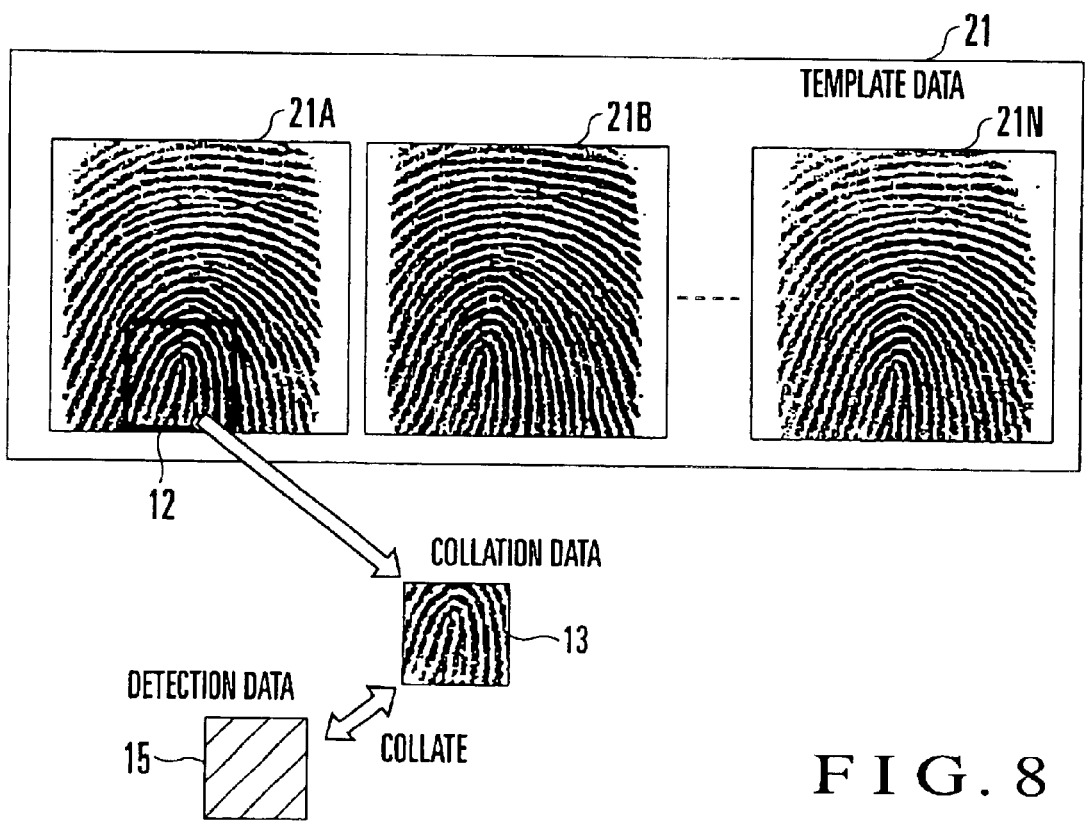
FIG. 8 is an explanatory view showing the basic recognition operation of the seventh embodiment.
Figure 9:
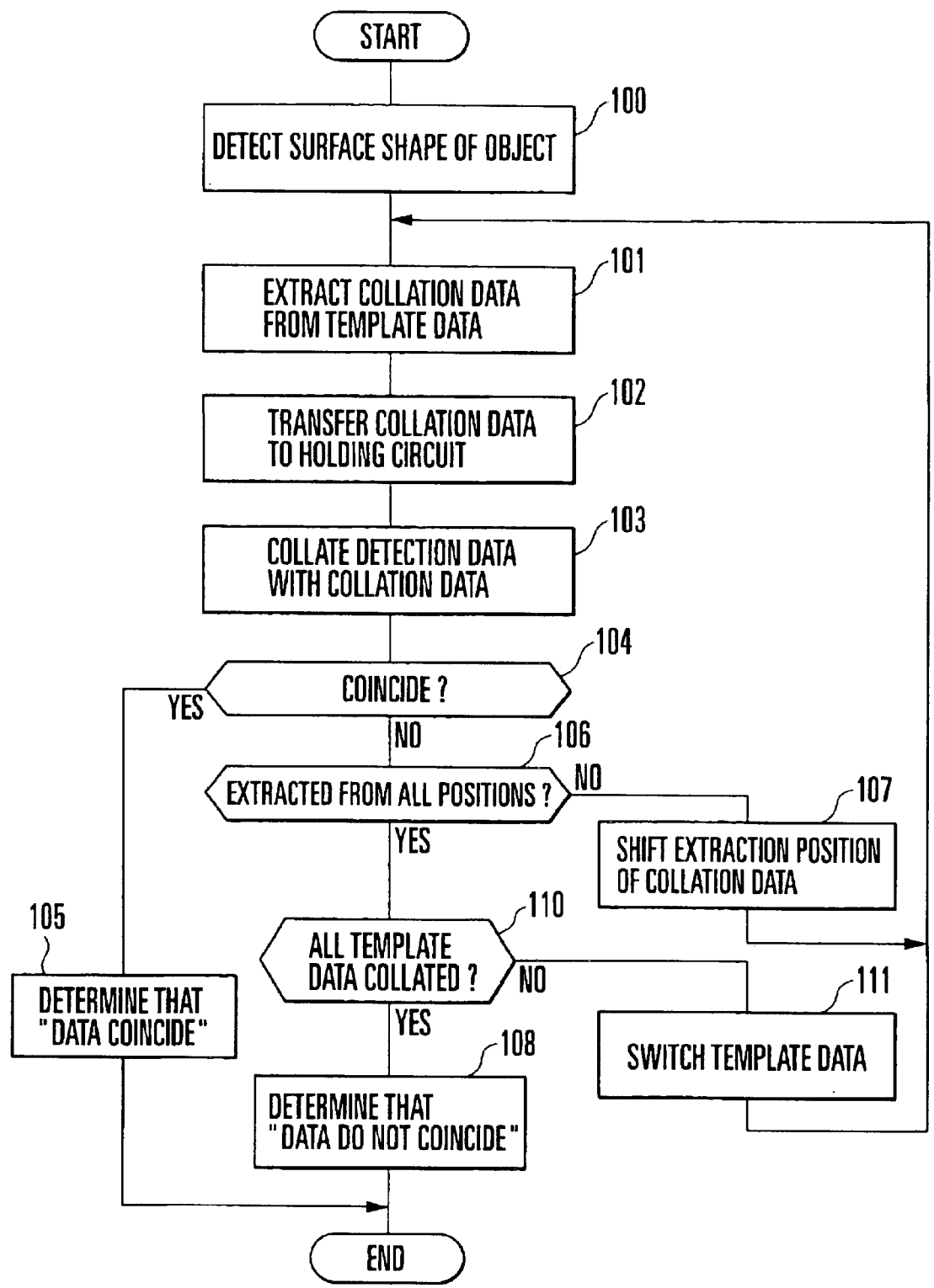
FIG. 9 is a flow chart showing the basic recognition operation of the seventh embodiment.

FIG. 8 shows the basic recognition operation of this embodiment. FIG. 9 shows the operation. In the above-described first to sixth embodiments, one template data is compared with an object. A case wherein a plurality of template data 21A to 21N are held in a storage circuit 9 in advance, and determination for authentication of an object is performed using these data will be described below. The same reference numerals as in FIG. 2 denote the same or equivalent parts in FIG. 9. In this embodiment, steps 110 and 111 are inserted between steps 106 and 108. The circuit arrangement is the same as in FIG. 1.

When it is determined that detection data detected from the object does not coincide with collation data extracted from template data (NO in step 104), and the collation data is extracted from all positions of the currently selected template data (YES in step 106), it is determined whether collation with all template data is ended (step 110). If uncollated template data remains (NO in step 110), the next template data is selected (step 111). The flow returns to step 101 to start collation with the selected template data.

If it is determined in step 110 that collation with all template data is ended (YES in step 110), the flow advances to step 108 to determine that all the template data do not coincide with the object, and the series of collation processes are ended. It may be determined in step 110 whether collation with not all template data but a predetermined number of template data is ended.

This arrangement for performing determination for authentication using a plurality of template data can be widely applied to determination for authentication. Detection data 15 of an object, which is obtained by a surface shape detection circuit 7, slightly changes depending on the degree of pressing the object against the surface shape detection circuit 7, so no same detection data 15 can always be obtained from one object. When a plurality of different template data obtained from one object are used for determination for authentication, the authentication rate can be improved, and high reliability can be obtained. Template data obtained from a plurality of different objects may be used for determination for authentication. In this case, determination for authentication of a plurality of objects can be executed at once in a short time.

The eighth embodiment of the present invention will be described below with reference to FIG. 10.

Figure 10:
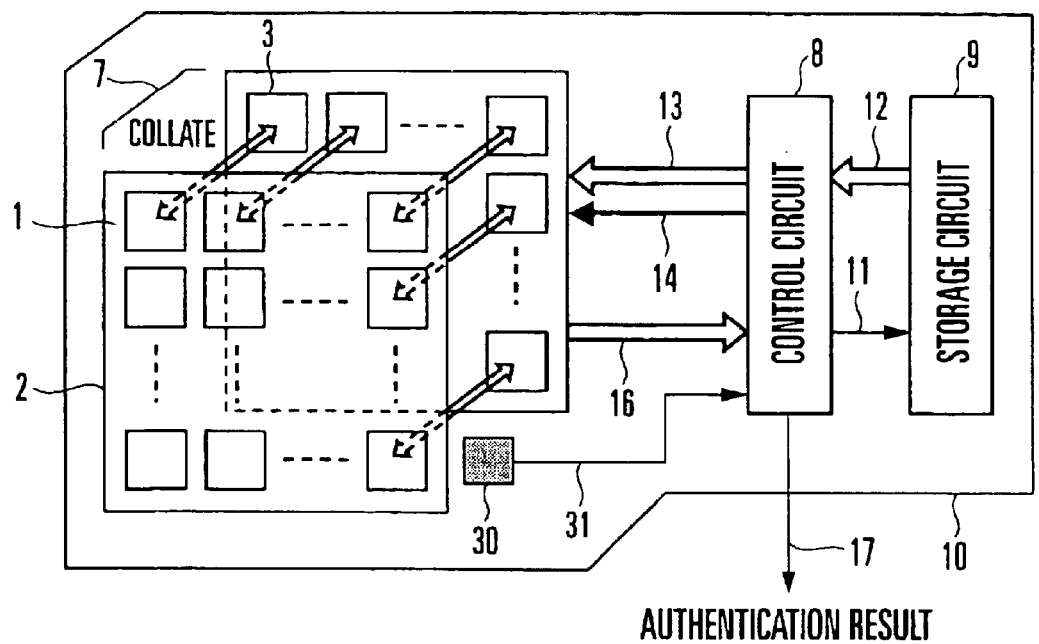
FIG. 10 is a block diagram of a surface shape recognition apparatus according to the eighth embodiment.

FIG. 10 shows a surface shape recognition apparatus of this embodiment. In this embodiment, in addition to the above-described circuit arrangement shown in FIG. 1, a contact sensor circuit 30 is located near a surface shape detection circuit 7, and the detection output from the contact sensor circuit 30 is input to a control circuit 8 as a timing signal 31. The contact sensor circuit 30 corresponds to a timing generation means (timing generation circuit).

In determination for authentication of an object, the object is pressed against the surface shape detection circuit 7. This contact state is detected by the contact sensor circuit 30, and the timing signal 31 is input to the control circuit 8. In accordance with this signal, the control circuit 8 outputs, to each signal processing circuit 3, a driving signal 14 for instructing to detect the target collation surface of the object, and authentication processing shown in FIG. 2 or 9 starts.

Since the surface shape detection circuit 7 is instructed to acquire detection data in accordance with the timing signal 31 from the contact sensor circuit 30, and determination for authentication of the object is performed using the obtained detection data, the data is extracted when the surface shape detection circuit 7 and object have an optimum positional relationship. For this reason, clear detection data can be obtained, and the authentication rate becomes high.

The ninth embodiment of the present invention will be described below with reference to FIGS. 11A to 11C.

Figure 11A:
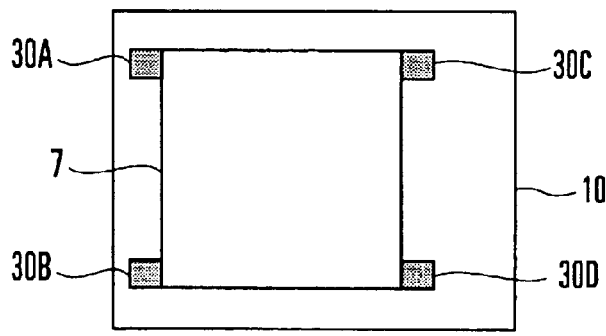
FIG. 11 is an explanatory view showing the basic recognition operation of the ninth embodiment.
Figure 11B:
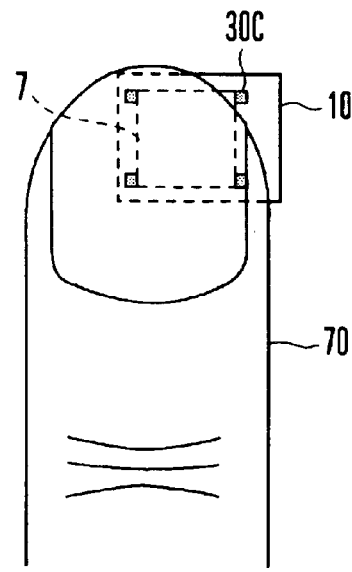
Figure 11C:
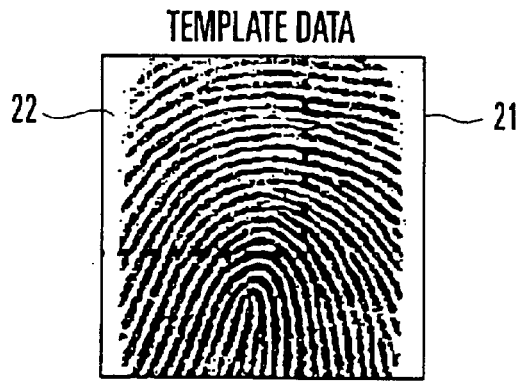

FIGS. 11A to 11C show the basic recognition operation of this embodiment. FIG. 11A shows the layout of contact sensor circuits, FIG. 11B shows a contact example of an object, and FIG. 11C shows a collation data extraction region. In the above-described eighth embodiment, one contact sensor circuit 30 is used. However, a plurality of contact sensor circuits 30A to 30D may be laid out around a surface shape detection circuit 7, as shown in FIG. 11A. When the detection outputs from the contact sensor circuits 30A to 30D are used, the positional relationship between an object and the surface shape detection circuit 7 can be grasped, so a region where collation data 12 is to be extracted from template data 21 can be limited. The contact sensor circuits 30A to 30D correspond to position detection circuits.

As shown in FIG. 11B, when detection outputs representing a contact state are input from the contact sensor circuits 30A, 30B, and 30D, and a detection output representing a noncontact state is input from the contact sensor circuit 30C to the control circuit 8, it can be determined that an object (finger) 70 is pressed against the lower left side of the surface shape detection circuit 7. On the basis of the sizes of the surface shape detection circuit 7 and template data 21, the control circuit 8 defines, on the template data 21, a region 22 that can be detected by the surface shape detection circuit 7. Hence, the collation data 12 is extracted from a position within the region 22.

Since a plurality of position detection circuits, e.g., contact sensor circuits are laid out around the surface shape detection circuit 7 to detect the positional relationship between the surface shape detection circuit 7 and the object, the region 22 where the collation data 12 is to be read from the template data 21 can be limited on the basis of the detected positional relationship, and the time required for collation can be largely shortened.

Figure 12:
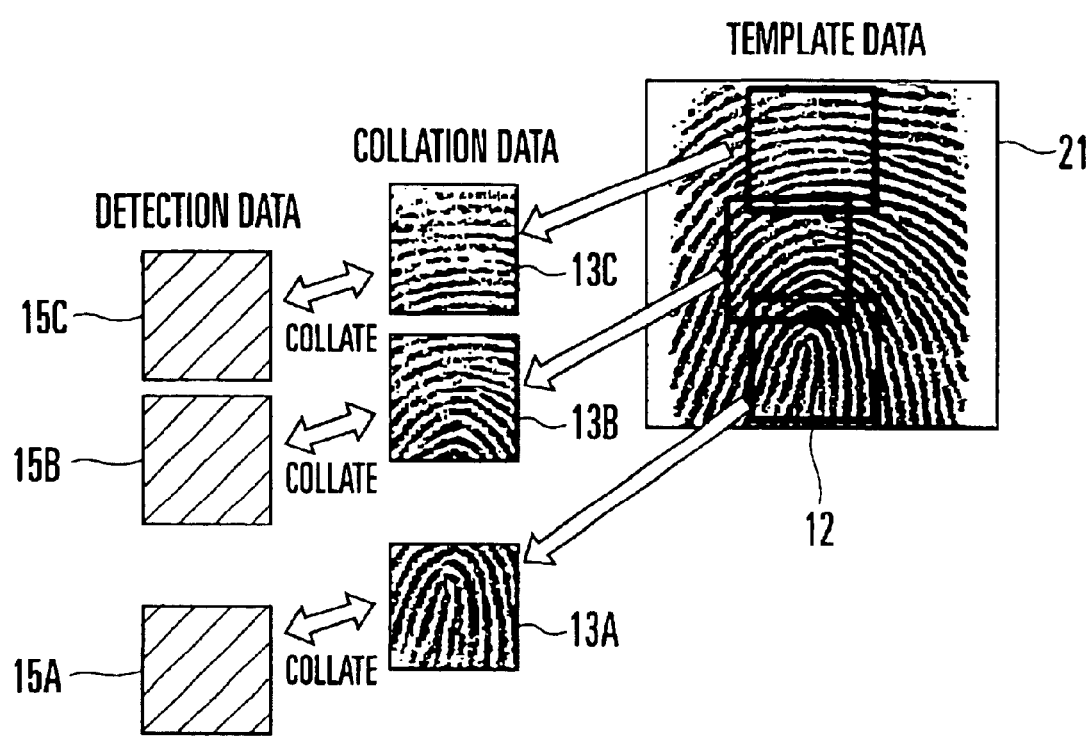
FIG. 12 is an explanatory view showing the basic recognition operation of the 10th embodiment.
Figure 13:
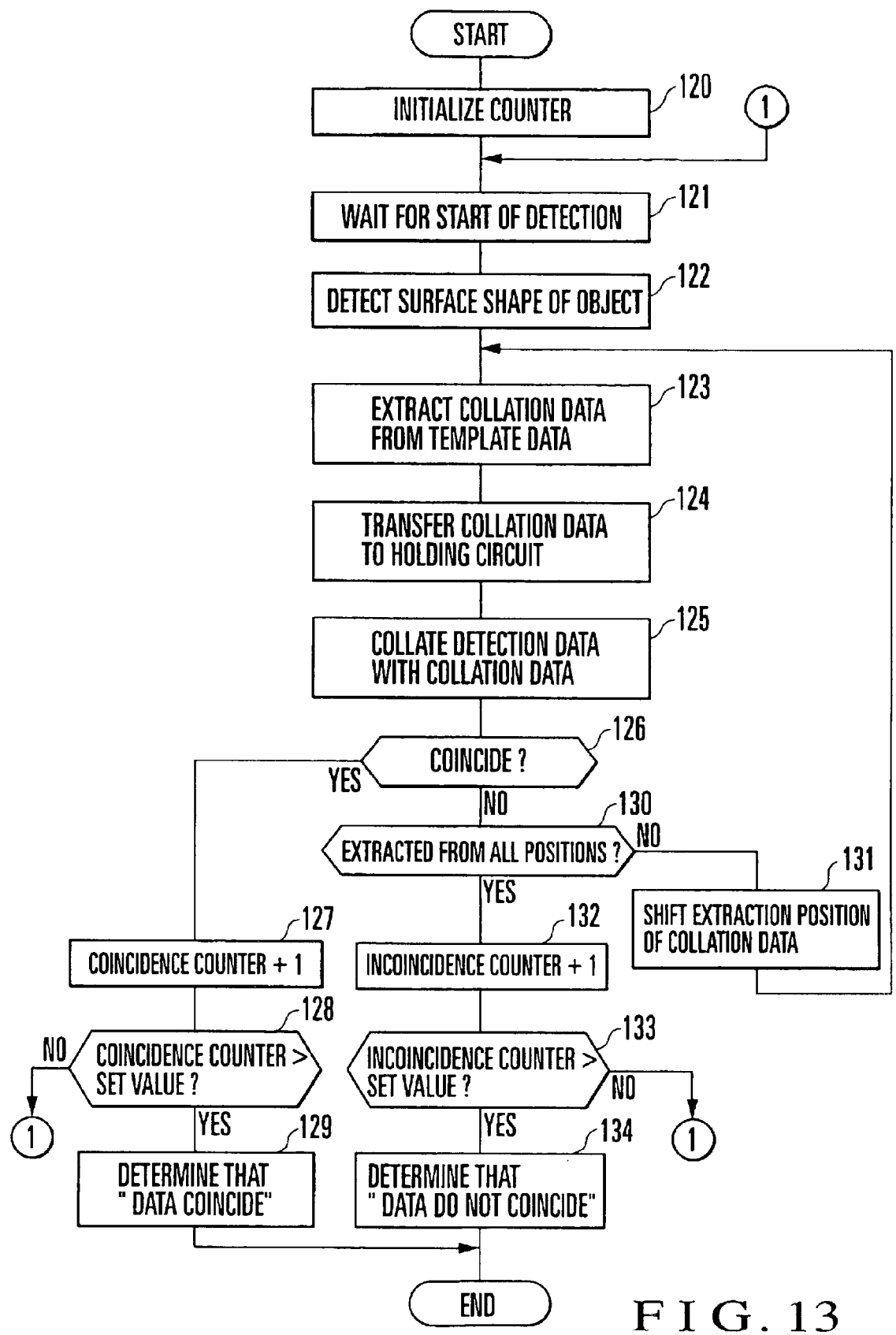
FIG. 13 is a flow chart showing the basic recognition operation of the 10th embodiment.

The 10th embodiment of the present invention will be described below with reference to FIGS. 12 and 13. FIG. 12 shows the basic recognition operation of this embodiment, and FIG. 13 shows the operation. In the above-described embodiments, one detection data detected from one object is collated with template data. A case wherein determination for authentication of an object is performed using a plurality of detection data detected from the object will be described below. In this case, a similarity representing the degree of similarity between the object and template data is used as the criterion of determination for authentication. The circuit arrangement is the same as in FIG. 10.

A control circuit 8 initializes the values of an internal coincidence counter and incoincidence counter which are prepared to obtain the similarity (step 120). Processing waits until a detection output representing an object contact state is input from a contact sensor circuit 30 (step 121). When the detection output changes to the object contact state, the control circuit 8 outputs, to each signal processing circuit 3, a driving signal 14 for instructing to detect the target collation surface of the object (step 122). Each signal processing circuit 3 processes a detection signal from a corresponding sensor element 1 and outputs detection data 15 on the basis of the driving signal 14.

The control circuit 8 extracts collation data 12 from an arbitrary position of template data 21 stored in a storage circuit 9 (step 123) and distributes the collation data 12, as collation data 13, to the signal processing circuits 3 in the surface shape detection circuit 7 in units of pixels corresponding to the sensor elements 1 (step 124).

In each signal processing circuit 3, a holding circuit 5 receives and holds the distributed collation data 13. A comparison circuit 6 compares and collates the detection data 15 from the sensor circuit 4 with the collation data 13 from the holding circuit 5 and outputs a comparison result 16 in units of pixels (step 125).

After that, the control circuit 8 totalizes the comparison results 16 from the signal processing circuits 3 and performs determination for collation of the object using a similarity formed from a predetermined statistic amount such as a total collation rate (step 126).

If the determination for collation represents coincidence between the two data (YES in step 126), the value of the coincidence counter is incremented by one (step 127), and the coincidence counter value is compared with a set value (step 128). When the coincidence counter value is larger than the set value (YES in step 128), it is determined that the object coincides with the template data 21 (step 129), and the series of collation processes are ended. If the coincidence counter value is equal to or smaller than the set value (NO in step 128), the flow returns to step 121 to detect new collation data in accordance with the next contact detection and repeat the collation processes.

When determination for authentication indicates that the two data do not coincide (NO in step 126), it is determined whether the collation data 13 has been extracted from all positions of the template data 21 (step 130). If an unextracted position still remains (NO in step 130), the collation data extraction position is shifted to the next position (step 131). The flow returns to step 123 to compare the collation data 13 extracted from the next position with the detection data 15.

If extraction from all positions is ended in step 130 (YES in step 130), the value of the incoincidence counter is incremented by one (step 132), and the incoincidence counter value is compared with the set value (step 133).

When the incoincidence counter value is larger than the set value (YES in step 133), it is determined that the object does not coincide with the template data 21 (step 134), and the series of collation processes are ended. If the incoincidence counter value is equal to or smaller than the set value (NO in step 133), the flow returns to step 121 to detect new collation data in accordance with the next contact detection and repeat the collation processes.

Since a plurality of detection data detected from one object are used for determination for authentication of the object, the authentication accuracy becomes high because the number of shape information obtained from the object increases, and consequently, the authentication rate can be improved, as compared to a case wherein detection data obtained from an arbitrary region of the object is used for determination for authentication. When a flaw, sweat, or dust is present at the position where the target collation surface of the object is detected by the surface shape detection circuit 7, the flaw, sweat, or dust is contained in the detection data as noise. Even when accurate determination for authentication fails because of such noise contained in detection data, application of this embodiment enables determination for authentication using another detection data. Hence, determination for authentication can be accurately performed.

Since determination for authentication is executed by comparing the coincidence and incoincidence counter values with set value, the degree of determination for authentication can be controlled by adjusting the set value. For example, in authenticating a fingerprint, the degree to identify the authentic person and the degree to exclude other people, i.e., the security level can be set by adjusting the set value. More specifically, when the set value is small, the authentic person can easily be identified though other people can also be easily accepted. That is, the security level is lowered. When the set value is large, it becomes difficult to identify the authentic person though other people can be more easily excluded. That is, the security level is raised. Individual set values may be prepared for the coincidence counter and incoincidence counter.

Figure 14:
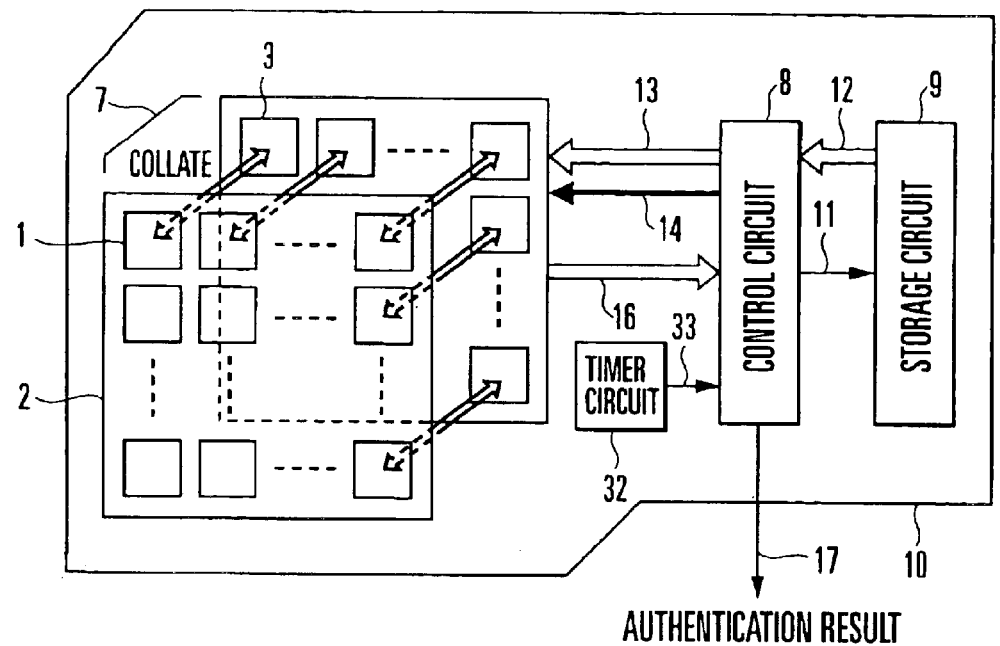
FIG. 14 is a block diagram of a surface shape recognition apparatus according to the 11th embodiment.
Figure 15:
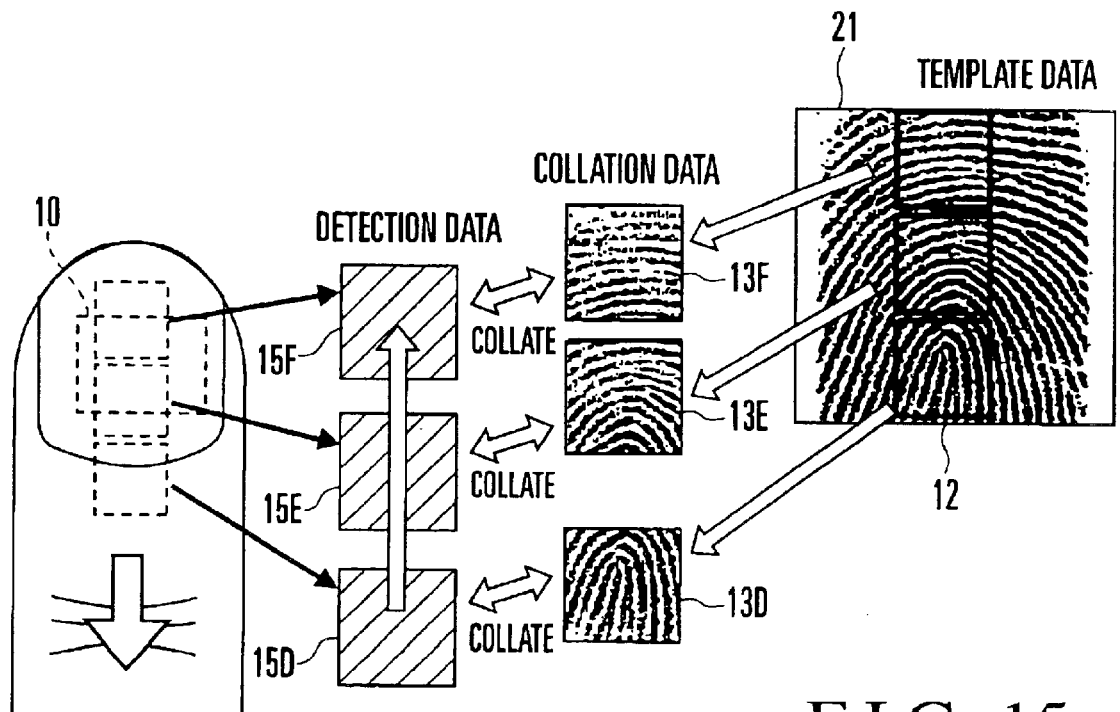
FIG. 15 is an explanatory view showing the basic recognition operation of the 11th embodiment.

The 11th embodiment of the present invention will be described below with reference to FIGS. 14 and 15. FIG. 14 shows a surface shape recognition apparatus of this embodiment, and FIG. 15 shows the basic operation thereof. A timer circuit 32 is added to the above-described circuit arrangement shown in FIG. 1. The timer circuit 32 outputs a timing signal 33 to a control circuit 8 every predetermined period. As the timer circuit 32, the internal timer of the control circuit 8 (for example, the internal timer of a CPU) may be used. The timer circuit 32 corresponds to a timing generation means (timing generation circuit).

The operation is the same as that of the above-described 10th embodiment (FIG. 13). In step 121, in accordance with the timing signal 33 from the timer circuit 32, i.e., every predetermined period, the control circuit 8 outputs, to each signal processing circuit 3, a driving signal 14 for instructing to detect the target collation surface of an object, and authentication processing between template data 21 and each detection data 15 is performed.

When the position of the object is moved on a surface shape detection circuit 7, detection data can be sequentially obtained from different positions, and the authentication accuracy can be further improved. Even when the position at which the object comes into contact with the surface shape detection circuit 7 is changed, as shown in FIG. 15, detection data at different positions can be obtained.

A scheme of detecting the surface shape of an object by moving the object kept in contact with a surface shape detection circuit 7 has been conventionally proposed (for example, Jeong-Woo Lee, Dong-Jin Min, Jiyoun Kim, and Wonchan Kim, "A 600-dpi Capacitive Fingerprint Sensor Chip and Image-Synthesis Technique", IEEE Journal of Solid-State Circuit, Vol. 34, No. 4, pp. 469–475, April 1999). In this scheme, a partial shape of an object is detected by moving the object while keeping it in contact with the surface shape detection circuit 7, the entire shape of the object is re-synthesized by image processing based on the plurality of detected data, and processing such as authentication is performed using the re-synthesized data. This method is substantially different from this embodiment wherein authentication processing is performed directly using partial detection data.

The 12th embodiment of the present invention will be described below with reference to FIG. 16. FIG. 16 shows a surface shape recognition apparatus of this embodiment. A moving sensor circuit 34 is added to the above-described circuit arrangement shown in FIG. 1. The moving sensor circuit 34 detects the moving amount of an object and outputs a timing signal 35 to a control circuit 8 in units of predetermined moving amounts. As the moving sensor circuit 34, a circuit for optically counting the number of density patterns, e.g., fingerprint patterns across the sensor is used. The moving sensor circuit 34 corresponds to a timing generation means (timing generation circuit).

The operation is the same as that of the above-described 10th embodiment (FIG. 13). In step 121, in accordance with the timing signal 35 from the moving sensor circuit 34, i.e., every predetermined period, the control circuit 8 outputs, to each signal processing circuit 3, a driving signal 14 for instructing to detect the target collation surface of an object, and authentication processing between template data 21 and each detection data 15 is performed. Hence, as in the 11th embodiment, when the position of the object is moved on a surface shape detection circuit 7, detection data can be sequentially obtained from different positions, and the authentication accuracy can be further improved.

The embodiments have been individually described above to help understanding the contents of the present invention. The embodiments may be combined as needed to obtain the above-described functions and effects. In the above-described embodiments, the detection data 15 obtained by the sensor element 1 and the collation data 12 (13) stored in the storage circuit 9 are two-dimensional surface shape data. However, these data are not limited to two-dimensional data. For example, even when these data are three-dimensional surface shape data including information in the depth direction of the three-dimensional pattern, the embodiments can be applied in the same way as described above, and the same functions and effects as described above can be obtained.

As has been described above, according to the present invention, a three-dimensional pattern in a partial region of the target collation surface of an object is electrically detected as detection data by a surface shape detection means formed from a plurality of sensor elements, template data representing the three-dimensional pattern of the entire target collation surface, which is obtained in advance from the object, is partially read out from an arbitrary position as collation data and compared with the detection data, and determination for authentication between the template data and the object is performed on the basis of the comparison result.

Hence, the surface area occupied by all sensor elements necessary for detecting the three-dimensional pattern of the target collation surface of the object can be reduced. This increases the yield in the process of manufacturing semiconductor integrated circuit devices and therefore reduces cost. In addition, high reliability can be ensured, unlike the conventional large-area device. For this reason, the surface shape of a human finger or animal nose having a small three-dimensional pattern can be recognized using a relatively small surface area, and cost reduction and high reliability can be ensured.

What is claimed is:

1. A surface shape recognition method of detecting a shape of a target collation surface of an object having a small surface shape pattern and comparing and collating the shape with predetermined data to authenticate the object, comprising the steps of:

electrically detecting the surface shape pattern in a partial region of the target collation surface of the object by surface shape detection means constructed by a plurality of sensor elements, partially reading out, as collation data, template data representing the surface shape pattern of the entire target collation surface, the template data being obtained from the object in advance, comparing the collation data with the detection data, and performing determination for authentication between the template data and the object on the basis of a comparison result, wherein the result of authenticaion is issued as data coincide at a particular point of time determination is made and scan processing and at said particular point of time when a result of said comparing shows coincidence, when said comparison result does not show coincidence, the position from which the template data is to be read out is changed to a different position, when the comparison is ended for all positions, the result of authentication is issued as data do not coincide and scan processing ends.

2. A method according to claim 1, further comprising sequentially partially reading out the template data from each position as the collation data, and performing determination for authentication of the object on the basis of the comparison result obtained for each collation data.

3. A method according to claim 2, further comprising storing a plurality of template data obtained from the object, and performing determination for authentication between the object and the plurality of template data.

4. A method according to claim 1, further comprising instructing said detection means to acquire the detection data in accordance with a predetermined timing signal, and performing determination for authentication of the object using the obtained detection data.

5. A method according to claim 4, further comprising using, as the timing signal, a signal output in accordance with contact between the object and said surface shape detection means.

6. A method according to claim 4, further comprising using, as the timing signal, a signal output every predetermined period.

7. A method according to claim 4, further comprising using, as the timing signal, a signal output in accordance with a moving amount of the object which moves while being kept in contact with said surface shape detection means.

8. An apparatus according to claim 4, wherein said timing generation means are formed on the same surface as the sensor elements, and where said timing signal is generated when the timing generation means has detected contact of said object.

9. An apparatus according to claim 4, wherein said timing signal is generated for every time set in advance.

10. An apparatus according to claim 4, wherein said timing generation means are coupled to the same surface as the plurality of sensor elements, said timing generation means counts ridges of the object that are sensed on the plurality of sensor elements to detect movement of the object, and the timing signal is generated for every predetermined amount of movement.

11. A method according to claim 1, further comprising detecting a position of the object relative to said surface shape detection means, and reading out the collation data from a corresponding region of the template data in accordance with the detected position of the object.

12. A method according to claim 1, further comprising detecting a plurality of detection data from the object, performing collation determination between the template data and each of the plurality of detection data, and performing determination for authentication of the object on the basis of each collation determination result.

13. A method according to claim 12, further comprising using, as the plurality of detection data, data individually detected from different positions of the object.

14. A method according to claim 13, further comprising counting the number of coincidences or incoincidences or the numbers of coincidences and incoincidences in the collation determination results between the detection data and the template data, and performing determination for authentication of the object on the basis of the counted number of coincidences or incoincidences.

15. A surface shape recognition apparatus for detecting a shape of a target collation surface of an object having a small surface shape pattern and comparing and collating the shape with predetermined data to authenticate the object, comprising:

detection means for electrically detecting the surface shape pattern in a partial region of the target collation surface of the object using a plurality of sensor elements and outputting detection data representing the surface shape pattern;

comparison means for comparing the detection data from said detection means with predetermined collation data and outputting a comparison result;

storage means for storing template data representing the surface shape pattern of the entire target collation surface, the template data being obtained from the object in advance; and control means for partially reading out, as collation data, the template data stored in said storage means from an arbitrary position, outputting the collation data to said comparison means, and performing determination for authentication between the template data and the object on the basis of the comparison result from said comparison means, wherein when said comparison result shows coincidence the control means issues the authentication data coincide at the particular point of time, and scan processing ends at said particular point of time, when said comparison result does not show coincidence, the position from which the template data is to be read out is changed to a different position, when the comparison is ended for all positions, the result of authentication is issued as data do not coincide and scan processing ends.

16. An apparatus according to claim 15, wherein said control means partially reads out, as the collation data, the template data from each position, sequentially outputs the collation data to said comparison means, and performs determination for authentication of the object on the basis of the comparison result obtained from said comparison means in units of collation data.

17. An apparatus according to claim 16, wherein
said storage means stores a plurality of template data obtained from the object, and
said control means performs determination for authentication between the object and the plurality of template data.

18. An apparatus according to claim 15, wherein
said apparatus further comprises timing generation means for outputting a predetermined timing signal, and
said control means instructs said detection means to acquire the detection data in accordance with the timing signal from said timing generation means and performs determination for authentication of the object using the obtained detection data.

19. An apparatus according to claim 18, wherein said timing generation means are formed on the same surface as the sensor elements, and where said timing signal is generated when the timing generation means has detected contact of said object.

20. An apparatus according to claim 18, wherein said timing signal is generated for every time set in advance.

21. An apparatus according to claim 18, wherein said timing generation means are coupled to the same surface as the plurality of sensor elements, said timing generation means counts ridges of the object that are sensed on the plurality of sensor elements to detect movement of the object, and the timing signal is generated for every predetermined amount of movement.

22. An apparatus according to claim 15, wherein
said apparatus further comprises position detection means for detecting a position of the object relative to said detection means, and
said control means reads out the collation data from a corresponding region of the template data in accordance with the position of the object detected by said position detection means.

23. An apparatus according to claim 15, wherein
said detection means detects a plurality of detection data from the object and outputs each detection data, and
said control means performs collation determination between the template data and each of the plurality of detection data and performs determination for authentication of the object on the basis of each collation determination result, wherein said control means increases a value of a coincidence counter when a comparison result is data coincide from the comparison to a certain detection data, when the value of the coincidence counter is larger than a predetermined value, the result of authentication is data coincide and processing ends, when the value of the coincidence counter is not larger than the predetermined value, the comparison processing to another detection data is performed, wherein when said comparison result is data do not coincide, the value of the incoincidence counter increases, and when the value of the incoincidence counter becomes larger than the predetermined value, the result of the authentication is data do not coincide and processing ends, and when the value of the incoincidence counter is less than the predetermined value, the comparison processing is performed to another detection data.

24. An apparatus according to claim 23, wherein said detection means individually detects detection data from different positions of the object and outputs the detection data.

25. A surface shape recognition apparatus for detecting a shape of a target collation surface of an object having a small surface shape pattern and comparing and collating the shape with predetermined data to authenticate the object, comprising:
a surface shape detection circuit for electrically detecting the surface shape pattern in a partial region of the target collation surface of the object, comparing detection data representing the surface shape pattern with predetermined collation data, and outputting a comparison result;
a storage circuit for storing template data representing the surface shape pattern of the entire target collation surface, the template data being obtained from the object in advance; and
a control circuit for partially reading out, as collation data, the template data stored in said storage circuit from an arbitrary position, outputting the collation data to said surface shape detection circuit, and performing determination for authentication of the object on the basis of the comparison result from said surface shape detection circuit, the control circuit issues the result of authentication as data coincide at a particular point of time determination is made and ends scan processing at said particular point of time when said comparison result shows coincidence,
said surface shape detection circuit comprising
a plurality of sensor elements arranged in correspondence with the partial region of the target collation surface of the object to electrically detect the surface shape pattern in the partial region and output a detection signal,
and a plurality of signal processing circuits each arranged in correspondence with one of said sensor elements to compare the detection data obtained from the detection signal of a corresponding sensor element with corresponding collation data and output a comparison result, wherein said template data is transmitted from said storage circuit to said plurality of signal processing circuits and collated.

26. An apparatus according to claim 25, wherein said control circuit partially reads out, as the collation data, the template data from each position and performs determination for authentication of the object on the basis of the comparison result between each collation data and the detection data.

27. An apparatus according to claim 26, wherein said storage circuit stores a plurality of template data obtained from the object, and
said control circuit performs determination for authentication between the object and the plurality of template data.

28. An apparatus according to claim 27, wherein said storage circuit stores a plurality of template data obtained from different objects.

29. An apparatus according to claim 25, wherein
said apparatus further comprises a timing generation circuit for outputting a predetermined timing signal, and
said control circuit instructs said surface shape detection circuit to acquire the detection data in accordance with the timing signal from said timing generation means and performs determination for authentication of the object using the obtained detection data.

30. An apparatus according to claim 29, wherein said timing generation circuit comprises a contact sensor circuit for detecting that the object comes into contact with said surface shape detection circuit and outputting the timing signal in accordance with the detection.

31. An apparatus according to claim 29, wherein said timing generation circuit comprises a timer circuit for outputting the timing signal every predetermined period.

32. An apparatus according to claim 29, wherein said timing generation circuit comprises a moving sensor circuit for detecting a moving amount of the object kept in contact with said surface shape detection circuit and outputting the timing signal in accordance with the moving amount,
wherein the moving amount is determined from ridges of a fingerprint crossing on said moving sensor circuit.

33. An apparatus according to claim 25, wherein
said apparatus further comprises a position detection circuit for detecting a position of the object relative to said surface shape detection circuit, and
said control circuit reads out the collation data from a corresponding region of the template data in accordance with the position of the object detected by said position detection circuit.

34. An apparatus according to claim 33, wherein said position detection circuit comprises a plurality of contact sensor circuits laid out around said surface shape detection circuit.

35. An apparatus according to claim 25, wherein
said surface shape detection circuit detects a plurality of detection data from the object and outputs each detection data, and
said control circuit performs collation determination between the template data and each of the plurality of detection data and performs determination for authentication of the object on the basis of each collation determination result.

36. An apparatus according to claim 35, wherein said surface shape detection circuit individually detects detection data from different positions of the object and outputs the detection data.

37. An apparatus according to claim 36, wherein said control circuit counts the number of coincidences or incoincidences or the numbers of coincidences and incoincidences in the collation determination results between the detection data and the template data and performs determination for authentication of the object on the basis of the counted number of coincidences or incoincidences.

38. An apparatus according to claim 25, wherein said circuits are formed on one chip as one semiconductor integrated circuit device.

39. An apparatus according to claim 25, wherein said circuits are separately formed on a plurality of chips which are mounted on one board.

40. An apparatus according to claim 25, wherein, of said circuits, at least said storage circuit is formed on a chip independently of the remaining circuits, and the chip of said storage circuit and chips of the remaining circuits are mounted on one board.

41. An apparatus according to claim 25, wherein a nonvolatile memory is used as said storage circuit.

42. An apparatus according to claim 25, wherein a total detection area for all of said sensor elements is smaller than a total target collation surface of the object.

43. An apparatus according to claim 42, wherein each of said signal processing circuits is arranged close to a corresponding sensor element, and an area occupied by all of said signal processing circuits is substantially not more than the total detection area for all of said sensor elements.

44. An apparatus according to claim 25, wherein as the template data, data detected by a large sensor having a detection area not less than a total target collation surface of the object is used.

45. An apparatus according to claim 44, wherein as the template data, data detected by an optical sensor or semiconductor sensor having a relatively large contact area is used.

46. An apparatus according to claim 25, wherein as the template data, data obtained by divisionally detecting the target collation surface using a sensor having a detection area smaller than a total target collation surface of the object to detect a plurality of segmented data and synthesizing the segmented data is used.

47. A surface shape recognition apparatus for detecting a shape of a target collation surface of an object having a small surface shape pattern and comparing and collating the shape with predetermined data to authenticate the object, comprising:
a surface shape detection circuit for electrically detecting the surface shape pattern in a partial region of the target collation surface of the object and outputting detection data representing the surface shape pattern;
a holding circuit for holding collation data to be compared with the detection data;
a comparison circuit for comparing the detection data from said surface shape detection circuit with the collation data in said holding circuit;
a storage circuit for storing template data representing the surface shape pattern of the entire target collation surface, the template data being obtained from the object in advance; and
a control circuit for partially reading out, as collation data, the template data stored in said storage circuit from an arbitrary position, outputting the collation data to said holding circuit, and performing determination for authentication of the object on the basis of a comparison result from said comparison circuit, the control circuit issues the result of authentication as data coincide at a particular point of time determination is made and ends scan processing at said particular point of time when said comparison result shows coincidence,
said surface shape detection circuit comprising
a plurality of sensor elements arranged in correspondence with the partial region of the target collation surface of the object to electrically detect the surface shape pattern in the partial region and output a detection signal, and
a plurality of signal processing circuits each arranged in correspondence with one of said sensor elements to output the detection data obtained from the detection signal of a corresponding sensor element,
wherein said template data is transmitted from said storage circuit to said plurality of signal processing circuits and collated.

48. An apparatus according to claim 47, wherein said control circuit partially reads out, as the collation data, the template data from each position and performs determination for authentication of the object on the basis of the comparison result between each collation data and the detection data.

49. An apparatus according to claim 48, wherein
said storage circuit stores a plurality of template data obtained from the object, and
said control circuit performs determination for authentication between the object and the plurality of template data.

50. An apparatus according to claim 49, wherein said storage circuit stores a plurality of template data obtained from different objects.

51. An apparatus according to claim 47, wherein
said apparatus further comprises a timing generation circuit for outputting a predetermined timing signal, and
said control circuit instructs said surface shape detection circuit to acquire the detection data in accordance with the timing signal from said timing generation means and performs determination for authentication of the object using the obtained detection data.

52. An apparatus according to claim 51, wherein said timing generation circuit comprises a contact sensor circuit for detecting that the object comes into contact with said surface shape detection circuit and outputting the timing signal in accordance with the detection.

53. An apparatus according to claim 51, wherein said timing generation circuit comprises a timer circuit for outputting the timing signal every predetermined period.

54. An apparatus according to claim 51, wherein said timing generation circuit comprises a moving sensor circuit for detecting a moving amount of the object kept in contact with said surface shape detection circuit and outputting the timing signal in accordance with the moving amount,
wherein the moving amount is determined from ridges of a fingerprint crossing on said sensor circuit.

55. An apparatus according to claim 47, wherein
said apparatus further comprises a position detection circuit for detecting a position of the object relative, to said surface shape detection circuit, and
said control circuit reads out the collation data from a corresponding region of the template data in accordance with the position of the object detected by said position detection circuit.

56. An apparatus according to claim 55, wherein said position detection circuit comprises a plurality of contact sensor circuits laid out around said surface shape detection circuit.

57. An apparatus according to claim 47, wherein
said surface shape detection circuit detects a plurality of detection data from the object and outputs each detection data, and
said control circuit performs collation determination between the template data and each of the plurality of detection data and performs determination for authentication of the object on the basis of each collation determination result.

58. An apparatus according to claim 57, wherein surface shape detection circuit individually detects detection data from different positions of the object and outputs the detection data.

59. An apparatus according to claim 58, wherein said control circuit counts the number of coincidences or incoincidences or the numbers of coincidences and incoincidences in the collation determination results between the detection data and the template data and performs determination for authentication of the object on the basis of the counted number of coincidences or incoincidences.

60. An apparatus according to claim 47, wherein said circuits are formed on one chip as one semiconductor integrated circuit device.

61. An apparatus according to claim 47, wherein said circuits are separately formed on a plurality of chips which are mounted on one board.

62. An apparatus according to claim 47, wherein, of said circuits, at least said storage circuit is formed on a chip independently of the remaining circuits, and the chip of said storage circuit and chips of the remaining circuits are mounted on one board.

63. An apparatus according to claim 47, wherein a RAM (Random Access Memory) is used as said holding circuit.

64. An apparatus according to claim 47, wherein a nonvolatile memory is used as said storage circuit.

65. An apparatus according to claim 47, wherein a total detection area for all of said sensor elements is smaller than a total target collation surface of the object.

66. An apparatus according to claim 65, wherein each of said signal processing circuits is arranged close to a corresponding sensor element, and an area occupied by all of said signal processing circuits is substantially not more than the total detection area for all of said sensor elements.

67. An apparatus according to claim 47, wherein as the template data, data detected by a large sensor having a detection area not less than a total target collation surface of the object is used.

68. An apparatus according to claim 67, wherein as the template data, data detected by an optical sensor or semiconductor sensor having a relatively large contact area is used.

69. An apparatus according to claim 47, wherein as the template data, data obtained by divisionally detecting the target collation surface using a sensor having a detection area smaller than a total target collation surface of the object to detect a plurality of segmented data and synthesizing the segmented data is used.

70. A surface shape recognition apparatus for detecting a shape of a target collation surface of an object having a small surface shape pattern and comparing and collating the shape with predetermined data to authenticate the object, comprising:
a surface shape detection circuit for electrically detecting the surface shape pattern in a partial region of the target collation surface of the object and outputting detection data representing the surface shape pattern;
a storage circuit for storing template data representing the surface shape pattern of the entire target collation surface, the template data being obtained from the object in advance; and
a control circuit for partially reading out, as collation data, the template data stored in said storage circuit from an arbitrary position, comparing the collation data with the detection data from said surface shape detection circuit, and performing determination for authentication of the object on the basis of a comparison result, the control circuit issues the result of authentication as data coincide at a particular point of time determination is made and ends scan processing at said particular point of time when said comparison result shows coincidence,
said surface shape detection circuit comprising
a plurality of sensor elements arranged in correspondence with the partial region of the target collation surface of the object to electrically detect the surface shape pattern in the partial region and output a detection signal, and
a plurality of signal processing circuits each arranged in correspondence with one of said sensor elements to output the detection data obtained from the detection signal of a corresponding sensor element,
wherein said template data is transmitted from said storage circuit to said plurality of signal processing circuits and collated.

71. An apparatus according to claim 70, wherein said control circuit partially reads out, as the collation data, the template data from each position and performs determination for authentication of the object on the basis of the comparison result between each collation data and the detection data.

72. An apparatus according to claim 71, wherein
said storage circuit stores a plurality of template data obtained from the object, and
said control circuit performs determination for authentication between the object and the plurality of template data.

73. An apparatus according to claim 72, wherein said storage circuit stores a plurality of template data obtained from different objects.

74. An apparatus according to claim 70, wherein
said apparatus further comprises a timing generation circuit for outputting a predetermined timing signal, and
said control circuit instructs said surface shape detection circuit to acquire the detection data in accordance with the timing signal from said timing generation means and performs determination for authentication of the object using the obtained detection data.

75. An apparatus according to claim 74, wherein said timing generation circuit comprises a contact sensor circuit for detecting that the object comes into contact with said surface shape detection circuit and outputting the timing signal in accordance with the detection.

76. An apparatus according to claim 74, wherein said timing generation circuit comprises a timer circuit for outputting the timing signal every predetermined period.

77. An apparatus according to claim 74, wherein said tuning generation circuit comprises a moving sensor circuit for detecting a moving amount of the object kept in contact with said surface shape detection circuit and outputting the timing signal in accordance with the moving amount,
wherein the moving amount is determined from ridges of a fingerprint crossing on said sensor circuit.

78. An apparatus according to claim 70, wherein
said apparatus further comprises a position detection circuit for detecting a position of the object relative to said surface shape detection circuit, and
said control circuit reads out the collation data from a corresponding region of the template data in accordance with the position of the object detected by said position detection circuit.

79. An apparatus according to claim 78, wherein said position detection circuit comprises a plurality of contact sensor circuits laid out around said surface shape detection circuit.

80. An apparatus according to claim 70, wherein
said surface shape detection circuit detects a plurality of detection data from the object and outputs each detection data, and
said control circuit performs collation determination between the template data and each of the plurality of detection data and performs determination for authentication of the object on the basis of each collation determination result.

81. An apparatus according to claim 80, wherein said surface shape detection circuit individually detects detection data from different positions of the object and outputs the detection data.

82. An apparatus according to claim 81, wherein said control circuit counts the number of coincidences or incoincidences or the numbers of coincidences and incoincidences in the collation determination results between the detection data and the template data and performs determination for authentication of the object on the basis of the counted number of coincidences or incoincidences.

83. An apparatus according to claim 70, wherein said circuits are formed on one chip as one semiconductor integrated circuit device.

84. An apparatus according to claim 70, wherein said circuits are separately formed on a plurality of chips which are mounted on one board.

85. An apparatus according to claim 70, wherein, of said circuits, at least said storage circuit is formed on a chip independently of the remaining circuits, and the chip of said storage circuit and chips of the remaining circuits are mounted on one board.

86. An apparatus according to claim 70, wherein a nonvolatile memory is used as said storage circuit.

87. An apparatus according to claim 70, wherein a total detection area for all of said sensor elements is smaller than a total target collation surface of the object.

88. An apparatus according to claim 87, wherein each of said signal processing circuits is arranged close to a corresponding sensor element, and an area occupied by all of said signal processing circuits is substantially not more than the total detection area for all of said sensor elements.

89. An apparatus according to claim 70, wherein as the template data, data detected by a large sensor having detection area not less than a total target collation surface of the object is used.

90. An apparatus according to claim 89, wherein as the template data, data detected by an optical sensor or semiconductor sensor having a relatively large contact area is used.

91. An apparatus according to claim 70, wherein as the template data, data obtained by divisionally detecting the target collation surface using a sensor having a detection area smaller than a total target collation surface of the object to detect a plurality of segmented data and synthesizing the segmented data is used.

* * * * *

UNITED STATES PATENT AND TRADEMARK OFFICE
CERTIFICATE OF CORRECTION

PATENT NO. : 6,917,694 B1
APPLICATION NO. : 09/573615
DATED : July 12, 2005
INVENTOR(S) : Machida et al.

It is certified that error appears in the above-identified patent and that said Letters Patent is hereby corrected as shown below:

On Title Page, Item [57], line 1, please insert -- a -- following "includes".

Col. 13, Line 25, Claim 1, line 16, please delete "authentiaion" and insert -- authentication --.

Signed and Sealed this

Sixth Day of November, 2007

JON W. DUDAS
*Director of the United States Patent and Trademark Office*